(12) United States Patent
Hayakawa et al.

(10) Patent No.: US 12,258,252 B2
(45) Date of Patent: Mar. 25, 2025

(54) DEODORIZING METHOD

(71) Applicant: Dai Nippon Printing Co., Ltd., Tokyo (JP)

(72) Inventors: Atsushi Hayakawa, Tokyo (JP); Tsubasa Tokimoto, Tokyo (JP); Ryuichi Tamagawa, Tokyo (JP); Syuta Ito, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 956 days.

(21) Appl. No.: 16/981,411

(22) PCT Filed: Mar. 28, 2019

(86) PCT No.: PCT/JP2019/013851
§ 371 (c)(1),
(2) Date: Sep. 16, 2020

(87) PCT Pub. No.: WO2019/189683
PCT Pub. Date: Oct. 3, 2019

(65) Prior Publication Data
US 2021/0009396 A1 Jan. 14, 2021

(30) Foreign Application Priority Data

Mar. 29, 2018 (JP) .................. 2018-065906
Mar. 29, 2018 (JP) .................. 2018-065920

(51) Int. Cl.
*A61L 2/04* (2006.01)
*A61L 2/18* (2006.01)
*B67C 3/00* (2006.01)

(52) U.S. Cl.
CPC ............. *B67C 3/001* (2013.01); *A61L 2/04* (2013.01); *A61L 2/18* (2013.01)

(58) Field of Classification Search
CPC .................................. A61L 2/04; A61L 2/18
See application file for complete search history.

(56) References Cited

U.S. PATENT DOCUMENTS

| 2010/0093589 A1 | 4/2010 | Yoshikawa et al. |
| 2012/0000492 A1 | 1/2012 | Katzenbächer et al. |

(Continued)

FOREIGN PATENT DOCUMENTS

| CN | 104718151 A | 6/2015 |
| CN | 104755411 A | 7/2015 |

(Continued)

OTHER PUBLICATIONS

"SPX Flow Technology, CIP and Sanitation of Process Plant, 2013, SPX Corporation" (Year: 2013).*

(Continued)

*Primary Examiner* — Donald R Spamer
(74) *Attorney, Agent, or Firm* — BURR PATENT LAW, PLLC

(57) ABSTRACT

A deodorizing method includes a first rinsing step of supplying first rinse water for a first circulation system to a first circulation system (25a) including at least a heat sterilizer (3) that heats a drink, a chemical circulation step of supplying and circulating a chemical for a first circulation system in the first circulation system (25a), and a second rinsing step of supplying second rinse water for a first circulation system to the first circulation system (25a). At the chemical circulation step, the chemical for a first circulation system is heated to a temperature of 70° C. or higher and 150° C. or lower in the first circulation system (25a).

5 Claims, 9 Drawing Sheets

(56) References Cited

U.S. PATENT DOCUMENTS

| | | |
|---|---|---|
| 2015/0298178 A1 | 10/2015 | Hayakawa |
| 2016/0121376 A1 | 5/2016 | Hayakawa et al. |
| 2016/0185584 A1 | 6/2016 | Hayakawa et al. |
| 2017/0057800 A1* | 3/2017 | McGowan ............... B01F 31/87 |
| 2017/0305731 A1* | 10/2017 | Kyle ........................ B67D 1/08 |
| 2019/0047836 A1 | 2/2019 | Takahashi et al. |
| 2020/0148522 A1 | 5/2020 | Hayakawa et al. |

FOREIGN PATENT DOCUMENTS

| | | |
|---|---|---|
| DE | 10 2011 002 102 A1 | 10/2011 |
| JP | H09-030597 A1 | 2/1997 |
| JP | 2005-200627 A | 7/2005 |
| JP | 2007-022600 A1 | 2/2007 |
| JP | 2015-006920 A1 | 1/2015 |
| JP | 2015-174692 A1 | 10/2015 |
| JP | 2017-114496 A | 6/2017 |
| WO | 2011/009546 A1 | 1/2011 |
| WO | 2014/077319 A1 | 5/2014 |
| WO | 2014/098058 A1 | 6/2014 |
| WO | 2017/135449 A1 | 8/2017 |

OTHER PUBLICATIONS

Japanese Office Action (Application No. 2018-065906) dated Jun. 4, 2019 (with English translation).

Japanese Office Action (Application No. 2018-065906) dated Nov. 29, 2019 (with English translation).

Japanese Office Action (Application No. 2018-065906) dated Jul. 31, 2020 (with English translation).

Japanese Office Action (Application No. 2018-065920) dated May 31, 2019 (with English translation).

Japanese Office Action (Application No. 2018-065920) dated Nov. 29, 2019 (with English translation).

Japanese Office Action (Application No. 2018-065920) dated Jul. 31, 2020 (with English translation).

International Search Report and Written Opinion (Application No. PCT/JP2019/013851) dated Jun. 4, 2019.

Extended European Search Report (Application No. 19774269.5) dated Nov. 23, 2021.

Chinese Office Action (Application No. 201980018300.3) dated Nov. 24, 2021 (with English translation).

Japanese Office Action (Application No. 2020-191991) dated Feb. 15, 2022 (with English translation).

Japanese Office Action (Application No. 2020-191991) dated Oct. 29, 2021 (with English translation).

Japanese Office Action (Application No. 2020-191999) dated Oct. 29, 2021 (with English translation).

Japanese Office Action (Application No. 2020-191982) dated Oct. 29, 2021 (with English translation).

English translation of International Preliminary Report on Patentability (Chapter I) (Application No. PCT/JP2019/013851) dated Oct. 8, 2020, 18 pages.

* cited by examiner

DEODORIZING METHOD

TECHNICAL FIELD

The present invention relates to a deodorizing method of deodorizing a filling system.

BACKGROUND ART

A filling system has been conventionally known as a system of filling a vessel such as a bottle with a drink, in which the drink itself is sterilized, and a surge tank, a pipe, a filling nozzle, and the like are also sterilized to make them aseptic. In such a filling system, when the type of drinks is changed, for example, a cleaning in place (CIP) process is performed and further a sterilizing in place (SIP) process is performed (for example, Patent Literature 1).

CIP is performed for the purpose of removing the residue or the like of the previous drink in a drink flow path or a drink tank. The CIP process is performed by passing a cleaning solution obtained by adding an alkaline chemical such as caustic soda to water and then passing a cleaning solution obtained by adding an acidic chemical to water in the drink flow path, for example.

SIP is performed for the purpose of sterilizing the drink flow path or the drink tank to make it aseptic. The SIP process is performed by passing heated steam or hot water in the flow path cleaned by CIP, for example.

However, in recent years, various drinks including, for example, mineral water, carbonated drinks, tea-based drinks, fruit drinks, coffee drinks, milk-based drinks, functional drinks, alcoholic drinks, and so-called energy drinks containing caffeine and arginine have been filled in such a filling system. In addition, such various drinks include drinks containing many flavors. Further, in some cases, a drink that does not contain any flavor such as mineral water is filled after a drink containing many flavors. Consequently, if a flavor remains in the drink flow path after CIP and SIP, the remaining flavor may be mixed with the next drink and the scent of the previous drink may be attached to the next drink. If the scent of the previous drink is attached to the next drink, it is necessary to perform CIP and SIP again, resulting in a significant degradation in productivity.

CITATION LIST

Patent Literature

Patent Literature 1: JP 2007-22600 A

The present invention has been made in view of such points, and an object of the invention is to provide a deodorizing method capable of efficiently removing a flavor remaining in a filling system.

SUMMARY OF INVENTION

According to the present invention, there is provided a deodorizing method of deodorizing a filling system by CIP, the deodorizing method comprising a first rinsing step of supplying first rinse water for a first circulation system to a first circulation system including at least a heat sterilizer that heats a drink, a chemical circulation step of supplying and circulating a chemical for a first circulation system in the first circulation system, and a second rinsing step of supplying second rinse water for a first circulation system to the first circulation system wherein, at the chemical circulation step, the chemical for a first circulation system is heated to a temperature of 70° C. or higher and 150° C. or lower in the first circulation system.

In the deodorizing method according to the present invention, at the chemical circulation step, time required to supply and circulate the chemical for a first circulation system in the first circulation system is 5 minutes or more and 60 minutes or less.

In the deodorizing method according to the present invention, at the second rinsing step, the second rinse water for a first circulation system is heated to a temperature of 70° C. or higher 150° C. or lower in the first circulation system.

In the deodorizing method according to the present invention, at the second rinsing step, time required to supply the second rinse water for a first circulation system to the first circulation system is 5 minutes or more and 60 minutes or less.

In the deodorizing method according to the present invention, at the first rinsing step, the first rinse water for a first circulation system is heated to a temperature of 30° C. or higher 100° C. or lower in the first circulation system.

In the deodorizing method according to the present invention, at the first rinsing step, time required to supply the first rinse water for a first circulation system to the first circulation system is 5 minutes or more and 30 minutes or less.

The deodorizing method according to the present invention further comprising a third rinsing step of supplying third rinse water for a first circulation system to the first circulation system, wherein at the third rinsing step, the third rinse water for a first circulation system is heated to a temperature of 30° C. or higher 100° C. or lower in the first circulation system.

In the deodorizing method according to the present invention, at the third rinsing step, time required to supply the third rinse water for a first circulation system to the first circulation system is 5 minutes or more and 120 minutes or less.

According to the present invention, there is provided a deodorizing method of deodorizing a filling system by CIP, the deodorizing method comprising a first rinsing step of supplying first rinse water for a second circulation system to a second circulation system including at least a filling device that fills a content in a vessel, a chemical circulation step of supplying and circulating a chemical for a second circulation system in the second circulation system, and a second rinsing step of supplying second rinse water for a second circulation system to the second circulation system wherein, at the second rinsing step, the second rinse water for a second circulation system is heated to a temperature of 40° C. or higher and 100° C. or lower in the second circulation system.

In the deodorizing method according to the present invention, at the second rinsing step, time required to supply the second rinse water for a second circulation system to the second circulation system is 5 minutes or more and 60 minutes or less.

In the deodorizing method according to the present invention, at the first rinsing step, the first rinse water for a second circulation system is heated to a temperature of 40° C. or higher 100° C. or lower in the second circulation system.

In the deodorizing method according to the present invention, at the first rinsing step, time required to supply the first rinse water for a second circulation system to the second circulation system is 5 minutes or more and 30 minutes or less.

The deodorizing method according to the present invention further comprising a third rinsing step of supplying third rinse water for a second circulation system to the second circulation system, wherein at the third rinsing step, the third rinse water for a second circulation system is heated to a temperature of 40° C. or higher 100° C. or lower in the second circulation system.

In the deodorizing method according to the present invention, at the third rinsing step, time required to supply the third rinse water for a second circulation system to the second circulation system is 5 minutes or more and 120 minutes or less.

In the deodorizing method according to the present invention, at the chemical circulation step, the chemical for a second circulation system is heated to a temperature of 70° C. or higher 150° C. or lower in the second circulation system.

In the deodorizing method according to the present invention, at the chemical circulation step, time required to supply and circulate the chemical for a second circulation system in the second circulation system is 5 minutes or more and 60 minutes or less.

According to the present invention, there is provided a deodorizing method of deodorizing a filling system, the deodorizing method comprising a first CIP step of performing CIP of a first circulation system including a product heating sterilizer that heats a drink, a first SIP step of performing SIP of the first circulation system, a second CIP step of performing CIP of a second circulation system including a filling device that fills a content in a vessel, a second SIP step of performing SIP of the second circulation system, and a deodorizing treatment step of performing a deodorizing treatment on the first circulation system and the second circulation system, wherein at the deodorizing treatment step, heated water is supplied to at least the second circulation system having been subjected to the second SIP step.

In the deodorizing method, the deodorizing treatment step includes a step of supplying water to the first circulation system having been subjected to the first SIP step, a step of heating the water supplied to the first circulation system by the product heating sterilizer, and a step of supplying the water heated by the product heating sterilizer to the second circulation system having been subjected to the second SIP step.

In the deodorizing method according to the present invention, at the step of heating the water supplied to the first circulation system by the product heating sterilizer, the water is heated to a temperature of 70° C. or higher 100° C. or lower.

In the deodorizing method according to the present invention, at the step of supplying water to the first circulation system having been subjected to the first SIP step, time required to supply the water to the first circulation system is 5 minutes or more and 120 minutes or less.

In the deodorizing method according to the present invention, at the step of supplying the water heated by the product heating sterilizer to the second circulation system having been subjected to the second SIP step, time required to supply the water to the second circulation system is 5 minutes or more and 120 minutes or less.

In the deodorizing method according to the present invention, the second circulation system includes a tank that stores a sterilized drink and a heat sterilizer for preparing aseptic water that is connected to a downstream side of the tank and prepares aseptic water, and the deodorizing treatment step includes a step of supplying water to the heat sterilizer for preparing aseptic water and heating the water, and a step of supplying the water heated by the heat sterilizer for preparing aseptic water to the second circulation system having been subjected to the second SIP step.

In the deodorizing method according to the present invention, at the step of supplying water to the heat sterilizer for preparing aseptic water and heating the water, the water is heated to a temperature of 70° C. or higher 100° C. or lower.

In the deodorizing method according to the present invention, at the step of supplying the water heated by the heat sterilizer for preparing aseptic water to the second circulation system having been subjected to the second SIP step, time required to supply the water to the second circulation system is 5 minutes or more and 120 minutes or less.

According to the present invention, a flavor remaining in the filling system can be efficiently removed.

DESCRIPTION OF EMBODIMENTS

First Embodiment

A first embodiment of the present invention will be described below with reference to the drawings. FIG. 1 to FIG. 5 illustrate the first embodiment of the present invention.

First, a filling system to which a deodorizing method according to the present embodiment is applied will be schematically described with reference to FIG. 1.

Figure 1:
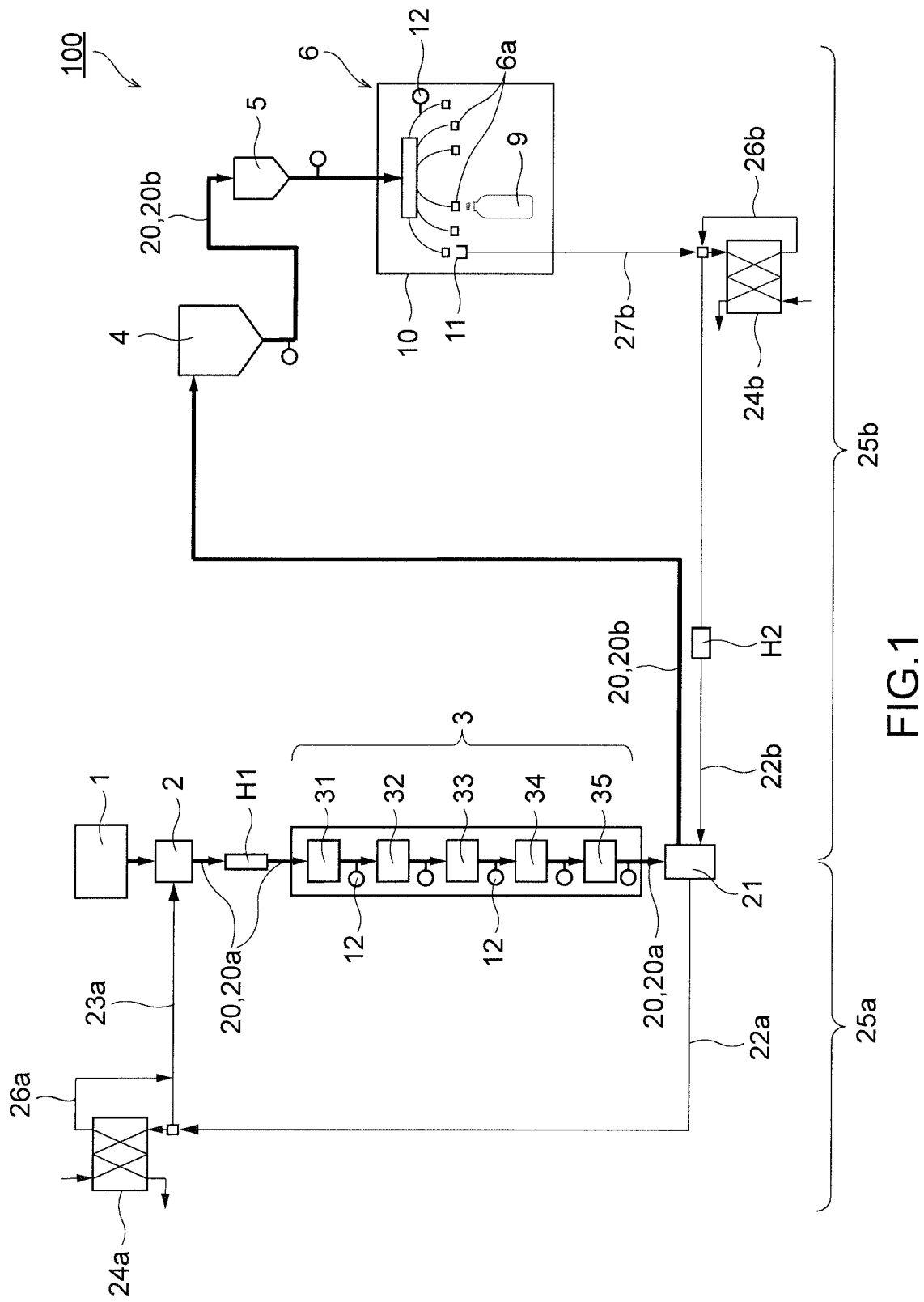
FIG. 1 is a block diagram illustrating a filling system to which a deodorizing method according to a first embodiment of the present invention is applied.

As illustrated in FIG. 1, a filling system 100 includes a preparation device 1, a balance tank 2, a heat sterilizer (product heating sterilizer) (Ultra High-temperature, hereinafter referred to as "UHT") 3, a surge tank 4, a surge tank for filler 5 and a filling device (filler) 6. The preparation device 1, the balance tank 2, the UHT 3, the surge tank (tank) 4, the surge tank for filler (tank) 5, and the filling device 6 are arranged in this order from an upstream side to a downstream side along a drink conveying direction. In addition, the preparation device 1, the balance tank 2, the UHT 3, the surge tank 4, the surge tank for filler 5, and the filling device 6 are connected to each other by a product supply system pipe 20 through which a drink passes, as will be described later. At least one of the surge tank 4 and the surge tank for filler 5 may be provided.

The preparation device 1 prepares a drink, which is a product, in a desired blending ratio. Examples of the product include mineral water, carbonated drinks, tea-based drinks, fruit drinks, coffee drinks, milk-based drinks, functional drinks, alcoholic drinks, and so-called energy drinks containing caffeine and arginine.

The balance tank 2 stores the drink prepared by the preparation device 1 to achieve a smooth flow of the drink. As illustrated in FIG. 1, a heater H1 is disposed on the downstream side of the balance tank 2 to heat a chemical in CIP to be described later.

The UHT 3 heats and sterilizes the drink supplied from the balance tank 2. This UHT 3 has a first-stage heating section 31, a second-stage heating section 32, a holding tube 33, a first-stage cooling section 34, and a second-stage cooling section 35. The drink supplied to the UHT 3 is gradually heated by the first-stage heating section 31 and the second-stage heating section 32, and then is heated to a target temperature in the holding tube 33. In this case, for example, the drink is heated to 60° C. or higher and 80° C. or lower by the first-stage heating section 31, and then is heated to 60° C. or higher and 150° C. or lower by the second-stage heating section 32. Further, the temperature of the drink is maintained in the holding tube 33 for a certain period of time. The drink having passed through the holding tube 33 is gradually cooled by the first-stage cooling section 34 and the second-stage cooling section 35. The number of stages of the heating section and the cooling section increases or decreases as necessary.

The surge tank 4 stores the drink sterilized by the UHT 3.

The surge tank for filler 5 stores the sterilized drink to be supplied to the filling device 6.

The filling device 6 fills a previously sterilized content from a mouth of a vessel 9 into the vessel 9. This filling device 6 fills the content into the empty vessel 9. In the filling device 6, while a plurality of the vessels 9 are rotated (revolved) with of filling nozzles 6a, the content is filled in the vessels 9. This content may be filled in the vessel 9 at room temperature. The content is previously sterilized by heating or the like, cooled to room temperature of 3° C. or higher and 40° C. or lower, and then filled in the vessel 9.

In addition, the filling system 100 includes an aseptic chamber 10. The filling device 6 described above is housed within the aseptic chamber 10. In this case, the inside of the aseptic chamber 10 is maintained in an aseptic state.

The preparation device 1, the balance tank 2, the UHT 3, the surge tank 4, the surge tank for filler 5, and the filling device 6, which have been described above, are connected to each other by the product supply system pipe 20 through which a drink passes. The product supply system pipe 20 includes an upstream-side supply pipe 20a located on the upstream side of a manifold valve 21 disposed between the UHT 3 and the surge tank 4, and a downstream-side supply pipe 20b located on the downstream side of the manifold valve 21. The manifold valve 21 switches a flow path. As indicated by thick lines in FIG. 1, the manifold valve 21 causes the upstream-side supply pipe 20a and the downstream-side supply pipe 20b to communicate with each other when the drink is filled in the vessel 9. On the other hand, when CIP and SIP (hereinafter, also referred to as "CIP and the like") are performed, the manifold valve 21 causes the upstream-side supply pipe 20a and an upstream-side return pipe 22a to be described later to communicate with each other (see FIG. 2 and FIG. 3), and causes the downstream-side supply pipe 20b and a downstream-side return pipe 22b to be described later to communicate with each other (see FIG. 4 and FIG. 5).

The upstream-side return pipe 22a is connected to the manifold valve 21, and a bypass pipe 23a connecting the upstream-side return pipe 22a to the balance tank 2 is connected to the downstream side of the upstream-side return pipe 22a. An upstream-side supply mechanism 24a to supply a chemical or the like at the time of CIP and the like is disposed on the downstream side of the bypass pipe 23a in the upstream-side return pipe 22a. An upstream-side introduction pipe 26a connecting the upstream-side supply mechanism 24a to the bypass pipe 23a is connected to the upstream-side supply mechanism 24a, and it is configured to supply a chemical or the like to the bypass pipe 23a through the upstream-side introduction pipe 26a. With such a configuration, the upstream-side supply pipe 20a, the upstream-side return pipe 22a, and the bypass pipe 23a constitute an upstream-side circulation system (first circulation system) 25a to perform CIP and the like. In the upstream-side circulation system 25a, a sealing member made of, for example, packing is provided at connection points of pipes, members, or the like so that a drink or the like does not leak out. In this case, various rubber including, for example, fluororesin (PTFE), EPDM, NBR, H-NBR, silicone rubber, fluorine-based rubber packing, and PTFE-coated rubber may be used as the sealing member in the upstream-side circulation system 25a.

An alkaline cleaning solution can be used as the chemical supplied to the bypass pipe 23a by the upstream-side supply mechanism 24a described above at the time of CIP. The alkaline cleaning solution contains, as an alkaline component, a desired one of chlorinated alkalis such as sodium hydroxide, potassium hydroxide, and sodium hypochlorite. The alkaline cleaning solution may contain organic acid such as citric acid, succinic acid, or gluconic acid, or phosphoric acid and alkaline metallic salts thereof, alkaline earth metallic salt, ammonium salt, metal ion sequestering agent such as hydroxyl carbonic acid compound such as alkanolamine salt such as ethylenediamine tetraacetate, anion surfactant, cationic surfactant, nonionic surfactant such as polyoxyethylenealkylphenylethers, solubilizing agent such as sodium cumene sulfonate, acid-based polymer such as polyacrylic acid or metallic salt thereof, corrosion inhibitor, preservative agent, anti-oxidator, disperser, antifoam agent, and the like. Water for dissolving these materials includes pure water, ion exchanging water, distilled water, tap water, and the like. The alkaline cleaning solution may also contain various bleaching agents such as hypochlorite, hydrogen peroxide, peracetic acid, sodium percarbonate, and thiourea dioxide.

Such an alkaline cleaning solution may contain, for example, sodium hydroxide or potassium hydroxide in an amount of 0.1% by mass or more and 10% by mass or less. The alkaline cleaning solution may contain sodium hypochlorite having a chlorine concentration of 100 to 3,000 ppm. When the cleaning solution containing sodium hypochlorite having a chlorine concentration of 100 to 3,000 ppm is used as the alkaline cleaning solution, the bactericidal property can be enhanced as compared with a case of using the cleaning solution containing sodium hydroxide.

Further, the downstream-side return pipe 22b including a heater H2 that heats a chemical or the like at the time of CIP and the like to be described later is connected to the manifold valve 21. A downstream-side supply mechanism 24b to supply a chemical or the like at the time of CIP and the like is disposed upstream of the downstream-side return pipe 22*b*. A downstream-side introduction pipe 26*b* connecting the downstream-side supply mechanism 24*b* to the downstream-side return pipe 22*b* is connected to the downstream-side supply mechanism 24*b*, and it is configured to supply a chemical or the like to the downstream-side return pipe 22*b* through the downstream-side introduction pipe 26*b*. Further, a drain pipe 27*b* that receives the chemical or the like having passed through the filling nozzles 6*a* of the filling device 6 described above during CIP and the like is connected to the downstream-side return pipe 22*b*. A cup 11 configured to be removable from each filling nozzle 6*a* is attached to the drain pipe 27*b*. The cup 11 is put on the filling nozzle 6*a* by an actuator (not illustrated) at the time of performing CIP and the like. The drain pipe 27*b* is thus connected to the filling nozzle 6*a*. With such a configuration, the downstream-side supply pipe 20*b*, the downstream-side return pipe 22*b*, and the drain pipe 27*b* constitute a downstream-side circulation system (second circulation system) 25*b* to perform CIP and the like. In the downstream-side circulation system 25*b*, a sealing member made of, for example, packing is provided at connection points of pipes, members, or the like so that a drink or the like does not leak out. In this case, various rubber including, for example, fluororesin (PTFE), EPDM, NBR, H-NBR, silicone rubber, fluorine-based rubber packing, and PTFE-coated rubber may also be used as the sealing member in the downstream-side circulation system 25*b*.

Alkaline cleaning solutions that are similar to those supplied to the bypass pipe 23*a* by the upstream-side supply mechanism 24*a* may be used in CIP and the like as the chemical supplied to the downstream-side return pipe 22*b* by the downstream-side supply mechanism 24*b* described above.

Temperature sensors 12 are connected to the upstream-side supply pipe 20*a*, the upstream-side return pipe 22*a*, the downstream-side supply pipe 20*b*, the downstream-side return pipe 22*b*, and the drain pipe 27*b* described above. The temperature sensor 12 may be disposed at, for example, a location where the temperature does not easily rise when hot water or the like is supplied therein. For example, as illustrated in FIG. 1, the temperature sensor 12 is disposed between the holding tube 33 and the first-stage cooling section 34 in the UHT 3, and the like. The temperature sensors 12 may be disposed at locations other than the upstream-side supply pipe 20*a*, the upstream-side return pipe 22*a*, the downstream-side supply pipe 20*b*, the downstream-side return pipe 22*b*, and the drain pipe 27*b*. For example, the temperature sensor 12 may be disposed in a flow path of the filling device 6 through which a content passes. Information about the temperatures measured by these temperature sensors 12 is transmitted to a control device (not illustrated).

The product supply system pipe 20 and the like described above include, in addition to the manifold valve 21 described above and an actuator (not illustrated), various switching valves, a pump, and the like, and these are also controlled by signals from the control device (not illustrated).

The filling system 100 described above may be a high temperature filling system that fills a content at a high temperature of 85° C. or higher and lower than 100° C. The filling system 100 may also be a medium temperature filling system that fills a content at a medium temperature of 55° C. or higher and lower than 85° C.

Next, an operation of the present embodiment will be described. A deodorizing method of deodorizing the filling system 100 by CIP will be described with reference to FIG. 2 to FIG. 5. In FIG. 2 to FIG. 5, pipes through which water and a chemical pass are indicated by thick lines.

First, after drink filling in the filling system 100 is completed, an operation button of a control device (not illustrated) is operated. As will be described later, CIP is performed in a predetermined procedure in the upstream-side circulation system 25*a* and the downstream-side circulation system 25*b* (see FIG. 2 to FIG. 5). At this time, the manifold valve 21 is switched, so that the upstream-side supply pipe 20*a* communicates with the upstream-side return pipe 22*a* (see FIG. 2 and FIG. 3), and the downstream-side supply pipe 20*b* communicates with the downstream-side return pipe 22*b* (see FIG. 4 and FIG. 5). CIP of the upstream-side circulation system 25*a* and CIP of the downstream-side circulation system 25*b* may be performed in sequence or in parallel with each other. CIP of the upstream-side circulation system 25*a* will be described first.

(First Rinsing Step)

Figure 2:
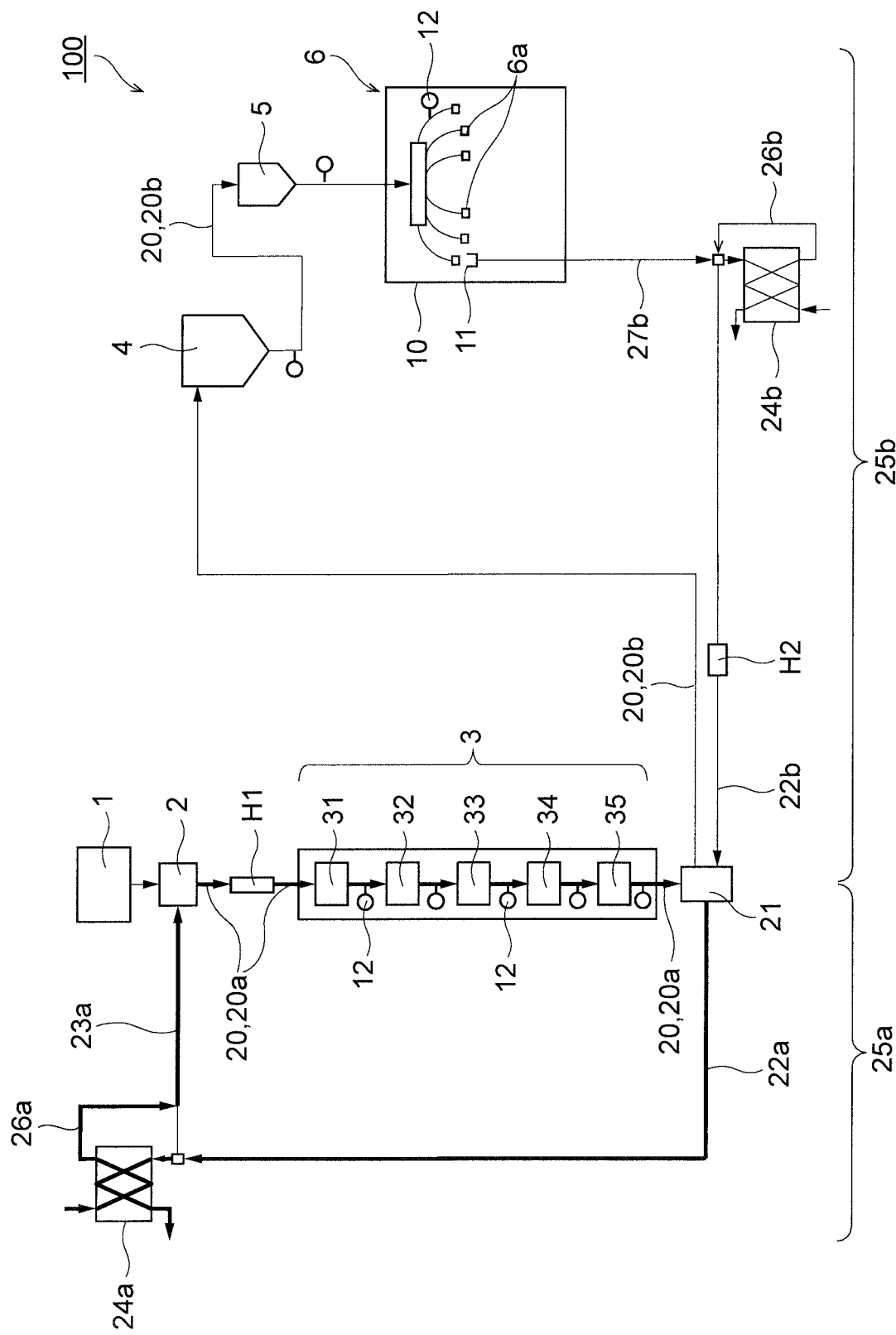
FIG. 2 is a block diagram illustrating the deodorizing method according to the first embodiment of the present invention.

As illustrated in FIG. 2, water (first rinse water for a first circulation system) is supplied to the upstream-side circulation system 25*a*. At this time, water is supplied first from the upstream-side supply mechanism 24*a* to the balance tank 2 through the upstream-side introduction pipe 26*a*. The water supplied to the balance tank 2 is sent to the UHT 3 through the upstream-side supply pipe 20*a* and heated by the UHT 3. At this time, the water is heated to a temperature of, for example, 30° C. or higher and 100° C. or lower, as an example, 50° C. As the water is heated to a temperature of 30° C. or higher, the previous drink remaining in the upstream-side circulation system 25*a* can be efficiently washed away. As a result, the flavor remaining in the upstream-side circulation system 25*a* can be efficiently removed at a chemical circulation step to be described later. Further, as the temperature of water is set to 100° C. or lower, energy saving and cost reduction can be achieved. At this time, water may be supplied to the balance tank 2 from a pipe or the like (not illustrated) without using the upstream-side supply mechanism 24*a*.

Next, the water heated by the UHT 3 flows in the upstream-side supply pipe 20*a* to pass through the manifold valve 21. The heated water is then supplied to the upstream-side return pipe 22*a*, passes through the upstream-side return pipe 22*a*, and is discharged as a waste solution from the upstream-side supply mechanism 24*a* to the outside. At this time, in the upstream-side supply mechanism 24*a*, heat exchange may be performed between water to be supplied and water to be discharged to the outside.

When water is supplied to the upstream-side circulation system 25*a* as described above, the time required to supply water to the upstream-side circulation system 25*a* may be 5 minutes or more and 30 minutes or less, as an example, 5 minutes. As the time required to supply water to the upstream-side circulation system 25*a* is 5 minutes or more, the previous drink remaining in the upstream-side circulation system 25*a* can be effectively washed away. Further, as the time required to supply water to the upstream-side circulation system 25*a* is 30 minutes or less, downtime can be reduced and energy saving can be achieved.

(Chemical Circulation Step)

Figure 3:
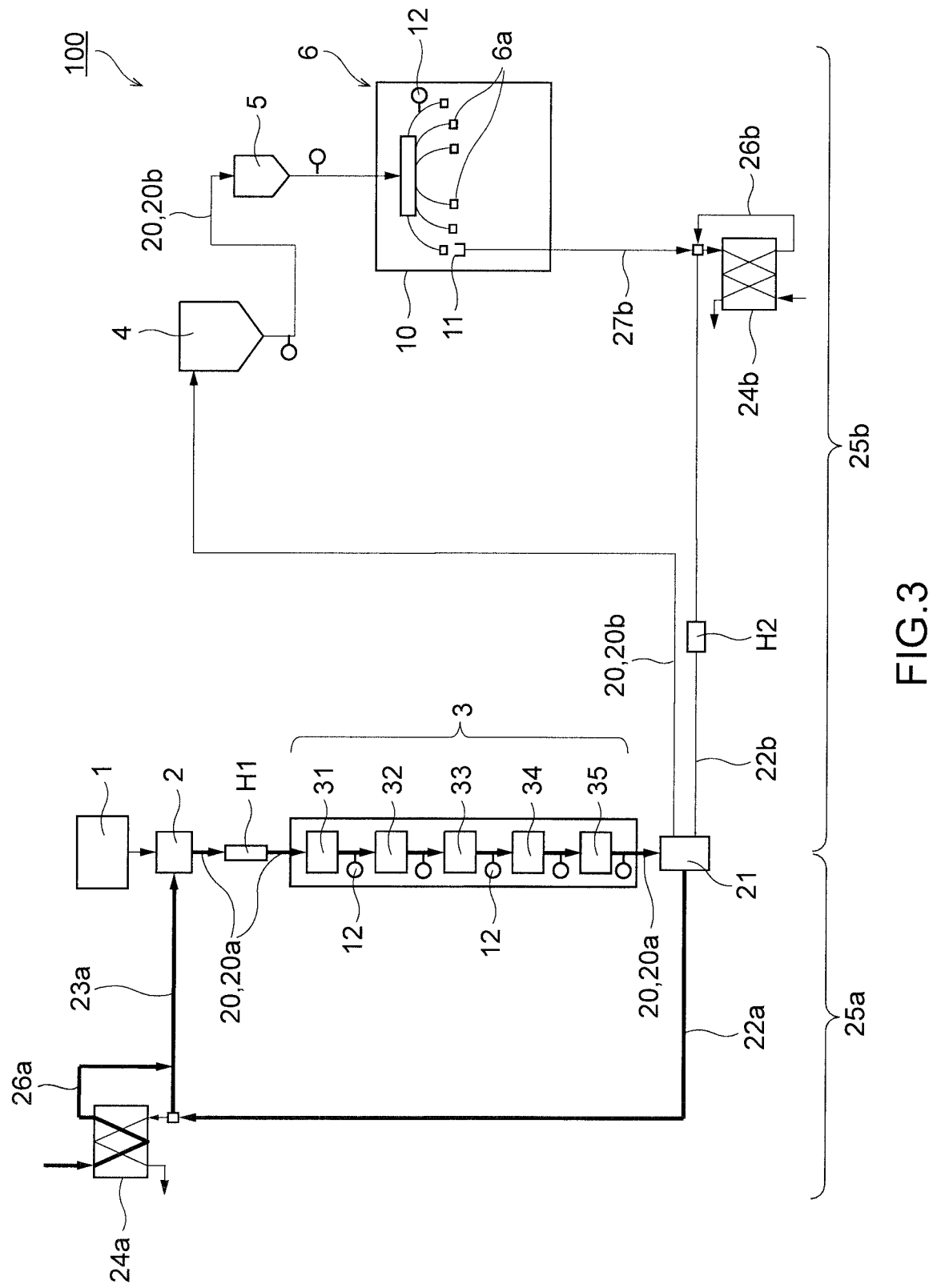
FIG. 3 is a block diagram illustrating the deodorizing method according to the first embodiment of the present invention.

Next, as illustrated in FIG. 3, a chemical (chemical for a first circulation system) is supplied and circulated in the upstream-side circulation system 25*a*. At this time, the chemical is supplied first from the upstream-side supply mechanism 24*a* to the balance tank 2 through the upstream-side introduction pipe 26*a*. In this case, an alkaline cleaning solution containing sodium hydroxide or potassium hydroxide in an amount of 0.1 to 10% by mass or an alkaline cleaning solution containing sodium hypochlorite having a chlorine concentration of 100 to 3,000 ppm may be used as the chemical. At this time, the chemical may be supplied to the balance tank 2 or the heater H1 from a pipe or the like (not illustrated) without using the upstream-side supply mechanism 24*a*.

The chemical supplied to the balance tank 2 passes through the balance tank 2 and is heated by the heater H1 disposed on the downstream side of the balance tank 2. The chemical heated by the heater Hi is sent to the UHT 3 through the upstream-side supply pipe 20*a* and further heated by the UHT 3. At this time, the chemical is heated to a temperature of, for example, 70° C. or higher and 150° C. or lower, preferably 90° C. or higher and 145° C. or lower, as an example, 140° C. As the chemical is heated to a temperature of 70° C. or higher, the flavor remaining in the upstream-side circulation system 25*a* can be efficiently removed. As the chemical is heated to a temperature of 90° C. or higher, the flavor remaining in the upstream-side circulation system 25*a* can be removed more efficiently. In addition, as the temperature of the chemical is set to 150° C. or lower, energy saving can be achieved. As the temperature of the chemical is set to 145° C. or lower, further energy saving can be achieved and heat damage to the pipes, members, and sealing members in the upstream-side circulation system 25*a* can be reduced. The chemical supplied to the balance tank 2 may be sent to the UHT 3 without being heated by the heater H1, and heated by the UHT 3.

Next, the heated chemical flows in the upstream-side supply pipe 20*a* to pass through the UHT 3 and the manifold valve 21. At this time, the heated chemical is supplied to the upstream-side return pipe 22*a* and then is supplied to the bypass pipe 23*a* connected to the upstream-side return pipe 22*a*. The chemical is then supplied into the balance tank 2 through the bypass pipe 23*a*. In this way, the chemical circulates in the upstream-side circulation system 25*a*. The chemical may be supplied to the heater H1 through the bypass pipe 23*a* by a pipe (not illustrated) or the like to circulate in the upstream-side circulation system 25*a*. The chemical circulates in the upstream-side circulation system 25*a* for a predetermined period of time, and then is discharged as a waste solution from the upstream-side supply mechanism 24*a* to the outside (see FIG. 2). In this case, the time required to supply and circulate the chemical in the upstream-side circulation system 25*a* may be 5 minutes or more and 60 minutes or less, and as an example, 15 minutes. As the time required to supply and circulate the chemical in the upstream-side circulation system 25*a* is 5 minutes or more, the flavor remaining in the upstream-side circulation system 25*a* can be effectively removed. Further, as the time required to supply and circulate the chemical in the first circulation system 25*a* is 60 minutes or less, downtime can be reduced and energy saving can be achieved.

Meanwhile, the preparation device 1 prepares, for example, a fruit drink or the like as a drink, as described above. Such drinks include drinks containing many flavors. Examples of the flavor include ethyl butyrate, ethyl 2-methylbutyrate, isoamyl acetate, limonene, ethyl caproate, isoamyl butyrate, hexyl acetate, allyl caproate, octyl aldehyde, decyl aldehyde, and the like. In particular, representative flavors include ethyl butyrate, ethyl 2-methylbutyrate, and limonene. In some cases, a drink that does not contain any flavor such as mineral water or green tea is filled after a drink containing these many flavors. At this time, if a flavor remains in the upstream-side circulation system 25*a*, the remaining flavor may be mixed with the next drink and the scent of the previous drink may be attached to the next drink.

In particular, for example, fluororesin packing is provided as a sealing member at connection points of pipes, members, or the like in the upstream-side circulation system 25*a*, as described above. Further, when a drink is filled in the vessel 9 (see FIG. 1), the drink is heated by the UHT 3 to a temperature of about 60° C. or higher and 150° C. or lower, as described above. At this time, the packing provided at the connection points of the pipes may thermally expand, resulting in a gap between each pipe and the packing. If a gap is formed between each pipe and the packing, the flavor may enter the gap. In this case, when the packing is cooled to contract, the flavor having entered the gap may be present between each pipe and the packing in a state of adhering to the packing. Further, it may be difficult to remove the flavor present between each pipe and the packing even if the chemical is supplied and circulated in the upstream-side circulation system 25*a*. Then, the flavor having entered such a gap may enter the next drink through the gap between each pipe and the packing, the gap resulting from the thermal expansion of the packing during the filling of the next drink.

According to the present embodiment, as the chemical is heated to a temperature of 70° C. or higher, the flavor remaining in the upstream-side circulation system 25*a* can be efficiently removed. That is, as the chemical is heated to a temperature of 70° C. or higher, the packing can be subjected to thermal expansion similar to thermal expansion that occurs when a drink is filled. This makes it possible to effectively remove the flavor having entered the gap due to the thermal expansion of the packing. It is thus possible to prevent the scent of the previous drink from being attached to the next drink. In this case, in order to achieve a higher deodorizing effect, it is effective to perform rinsing with water at a temperature higher than or equal to the sterilization temperature of the previous product. Further, as the chemical is heated to a temperature of 70° C. or higher, and supplied and circulated in the upstream-side circulation system 25*a* for 5 minutes or more, the pipes and members in the upstream-side circulation system 25*a* can be sterilized. This makes it possible to omit SIP, which is usually performed after CIP. Downtime can thus be reduced.

If necessary, cleaning with an acidic cleaning solution may be performed before and after cleaning with an alkaline cleaning solution. Further, for example, the cleaning with the acidic cleaning solution may be performed first, followed by the cleaning with the alkaline cleaning solution, and then the cleaning with the acidic cleaning solution may be performed. Alternatively, the cleaning with the alkaline cleaning solution may be performed first, followed by the cleaning with the acidic cleaning solution, and then the cleaning with the alkaline cleaning solution may be performed.

(Second Rinsing Step)

Next, as illustrated in FIG. 2, water (second rinse water for a first circulation system) is supplied to the upstream-side circulation system 25*a*. At this time, water is supplied to the upstream-side circulation system 25*a* as in the first rinsing step described above. In this case, water is heated to a temperature of, for example, 70° C. or higher and 150° C. or lower, as an example, 140° C. in the upstream-side circulation system 25*a*. As water is heated to a temperature of 70° C. or higher, the flavor remaining in the upstream-side circulation system 25*a* can be efficiently removed. That is, the flavors described above include water-soluble flavors such as ethyl butyrate and ethyl 2-methylbutyrate. In this case, as water is heated to a temperature of 70° C. or higher, the water-soluble flavor remaining in the upstream-side circulation system 25a can be efficiently removed. The deodorizing effect can thus be enhanced. Further, in this case, as water is heated to a temperature of 70° C. or higher, the flavor having entered the gap formed when the packing is thermally expanded can be removed, as described in the chemical circulation step. Further, as the temperature of water is set to 150° C. or lower, energy saving can be achieved. Also in this time, water may be supplied to the balance tank 2 from a pipe or the like (not illustrated) without using the upstream-side supply mechanism 24a.

The time required to supply water to the upstream-side circulation system 25a may be 5 minutes or more and 60 minutes or less, and as an example, 10 minutes. As the time required to supply water to the upstream-side circulation system 25a is 5 minutes or more, the flavor remaining in the upstream-side circulation system 25a can be effectively removed. Further, as the time required to supply water to the upstream-side circulation system 25a is 60 minutes or less, downtime can be reduced and energy saving can be achieved.

(Third Rinsing Step)

Further, if necessary, water (third rinse water for a first circulation system) may be supplied to the upstream-side circulation system 25a after the second rinsing step described above. At this time, water is supplied to the upstream-side circulation system 25a as in the first rinsing step and the second rinsing step described above. In this case, water is heated to a temperature of, for example, 30° C. or higher and 100° C. or lower, as an example, 40° C. in the upstream-side circulation system 25a. As water is heated to a temperature of 30° C. or higher, the water-soluble flavor remaining in the upstream-side circulation system 25a can be removed more efficiently and the deodorizing effect can be enhanced. Further, as the temperature of water is set to 100° C. or lower, energy saving and cost reduction can be achieved. Also in this time, water may be supplied to the balance tank 2 from a pipe or the like (not illustrated) without using the upstream-side supply mechanism 24a.

The time required to supply water to the upstream-side circulation system 25a may be 5 minutes or more and 120 minutes or less, and as an example, 10 minutes. As the time required to supply water to the upstream-side circulation system 25a is 5 minutes or more, the flavor remaining in the upstream-side circulation system 25a can be removed more effectively and the deodorizing effect can be enhanced. Further, as the time required to supply water to the upstream-side circulation system 25a is 120 minutes or less, downtime can be reduced and energy saving can be achieved.

In this way, CIP is performed in the upstream-side circulation system 25a, the flavor remaining in the upstream-side circulation system 25a is removed by CIP, and the upstream-side circulation system 25a is deodorized.

Next, CIP of the downstream-side circulation system 25b will be described.

Figure 4:
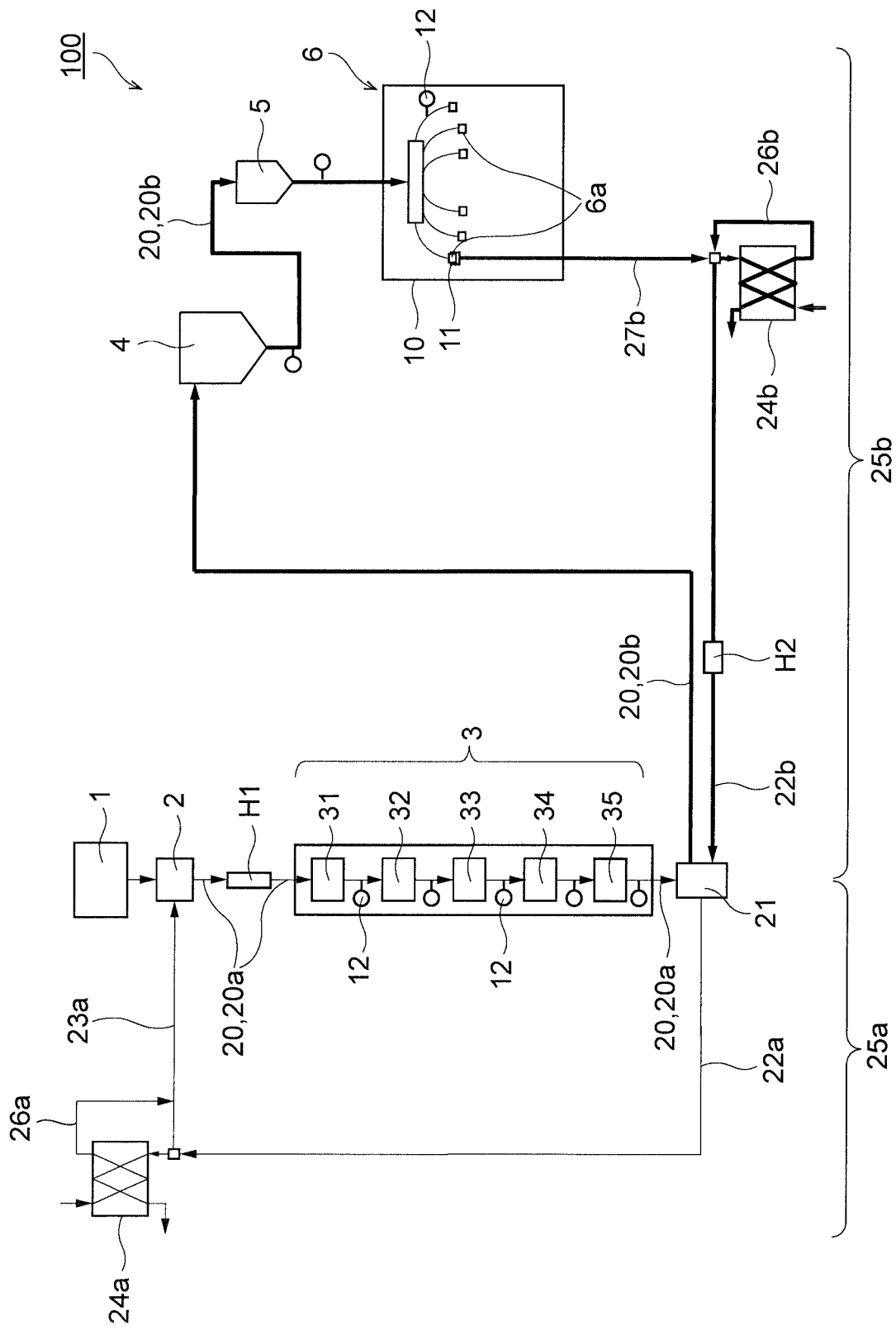
FIG. 4 is a block diagram illustrating the deodorizing method according to the first embodiment of the present invention.

As illustrated in FIG. 4, the cup 11 is first put on the filling nozzle 6a. The drain pipe 27b is thus connected to the filling nozzle 6a.

(First Rinsing Step)

Next, water (first rinse water for a second circulation system) is supplied to the downstream-side circulation system 25b. At this time, water is supplied first from the downstream-side supply mechanism 24b to the downstream-side return pipe 22b through the downstream-side introduction pipe 26b. The water supplied to the downstream-side return pipe 22b is heated by the heater H2. At this time, the water is heated to a temperature of, for example, 40° C. or higher and 100° C. or lower, as an example, 40° C. As the water is heated to a temperature of 40° C. or higher, the previous drink remaining in the downstream-side circulation system 25b can be efficiently washed away. As a result, flavor remaining in the downstream-side circulation system 25b can be efficiently removed at a chemical circulation step to be described later. Further, as the temperature of water is set to 100° C. or lower, energy saving and cost reduction can be achieved.

Next, the heated water flows in the downstream-side return pipe 22b to pass through the manifold valve 21. At this time, the heated water is supplied to the downstream-side supply pipe 20b, passes through the downstream-side supply pipe 20b, the surge tank 4, the surge tank for filler 5, the filling device 6, and the drain pipe 27b, and is discharged as a waste solution from the downstream-side supply mechanism 24b to the outside.

When water is supplied to the downstream-side circulation system 25b as described above, the time required to supply water to the downstream-side circulation system 25b may be 5 minutes or more and 30 minutes or less, as an example, 5 minutes. As the time required to supply water to the downstream-side circulation system 25b is 5 minutes or more, the previous drink remaining in the downstream-side circulation system 25b can be effectively washed away. Further, as the time required to supply water to the downstream-side circulation system 25b is 30 minutes or less, downtime can be reduced and energy saving can be achieved.

(Chemical Circulation Step)

Figure 5:
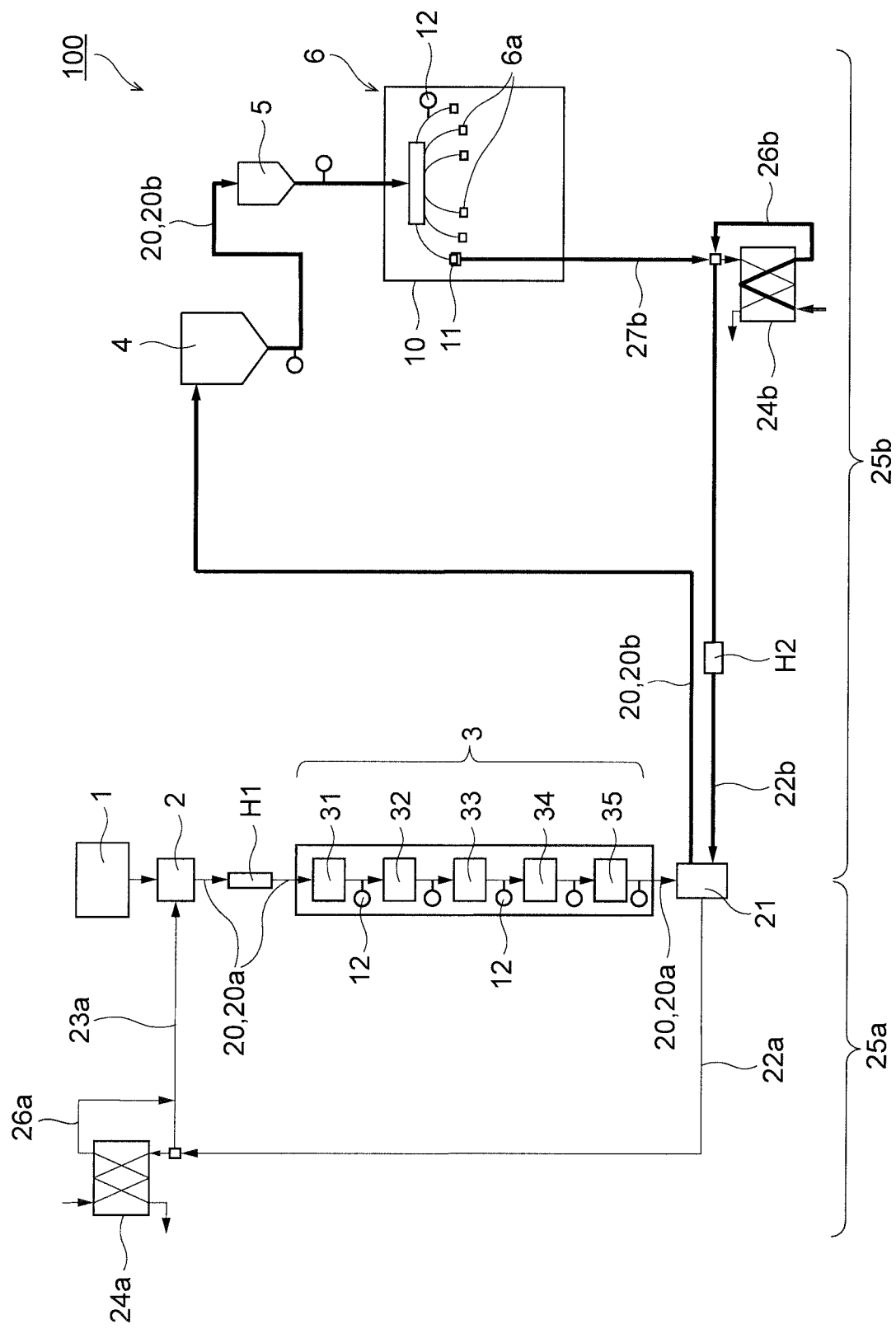
FIG. 5 is a block diagram illustrating the deodorizing method according to the first embodiment of the present invention.

Next, as illustrated in FIG. 5, a chemical (chemical for a second circulation system) is supplied and circulated in the downstream-side circulation system 25b. At this time, the chemical is supplied first from the downstream-side supply mechanism 24b to the downstream-side return pipe 22b through the downstream-side introduction pipe 26b. The alkaline cleaning solution similar to the chemical used when CIP is performed in the upstream-side circulation system 25a can be used as the chemical. The chemical supplied to the downstream-side return pipe 22b is heated by the heater H2. At this time, the chemical is heated to a temperature of, for example, 70° C. or higher and 100° C. or lower, as an example, 80° C. As the chemical is heated to a temperature of 70° C. or higher, the flavor remaining in the downstream-side circulation system 25b can be removed. Further, as the temperature of the chemical is set to 100° C. or lower, energy saving and cost reduction can be achieved. Further, in this case, as the chemical is heated to a temperature of 70° C. or higher as in the case of the upstream-side circulation system 25a described above, the flavor having entered the gap formed when the packing is thermally expanded can be effectively removed, and it is possible to prevent the scent of the previous drink from being attached to the next drink. In particular, packing made of ethylene propylene diene rubber (EPDM) may be used in the downstream-side circulation system 25b. Flavors tend to adhere to ethylene propylene diene rubber, and flavors tend to remain in the downstream-side circulation system 25b. The flavor adhering to the packing can be effectively removed by heating the chemical to a temperature of 70° C. or higher. Further, as the chemical is heated to a temperature of 70° C. or higher, and supplied and circulated in the downstream-side circulation system 25b for 5 minutes or more, SIP can be omitted and downtime can be reduced.

Next, the heated chemical passes through the manifold valve 21, and then passes through the downstream-side supply pipe 20b, the surge tank 4, the surge tank for filler 5, and the filling device 6. The chemical is then supplied to the downstream-side return pipe 22*b* through the drain pipe 27*b*. In this way, the chemical circulates in the downstream-side circulation system 25*b*. The chemical circulates in the downstream-side circulation system 25*b* for a predetermined period of time, and then is discharged as a waste solution from the downstream-side supply mechanism 24*b* to the outside (see FIG. 4). In this case, the time required to supply and circulate the chemical in the downstream-side circulation system 25*b* may be 5 minutes or more and 60 minutes or less, and as an example, 15 minutes. As the time required to supply and circulate the chemical in the downstream-side circulation system 25*b* is 5 minutes or more, the flavor remaining in the downstream-side circulation system 25*b* can be effectively removed. Further, as the time required to supply and circulate the chemical in the downstream-side circulation system 25*b* is 60 minutes or less, downtime can be reduced and energy saving can be achieved.

If necessary, cleaning with an acidic cleaning solution may be performed before and after cleaning with an alkaline cleaning solution, as in the upstream-side circulation system 25*a*. Further, for example, the cleaning with the acidic cleaning solution may be performed first, followed by the cleaning with the alkaline cleaning solution, and then the cleaning with the acidic cleaning solution may be performed. Alternatively, the cleaning with the alkaline cleaning solution may be performed first, followed by the cleaning with the acidic cleaning solution, and then the cleaning with the alkaline cleaning solution may be performed.

(Second Rinsing Step)

Next, as illustrated in FIG. 4, water (second rinse water for a second circulation system) is supplied to the downstream-side circulation system 25*b*. At this time, water is supplied to the downstream-side circulation system 25*b* as in the first rinsing step in the downstream-side circulation system 25*b* described above. In this case, water is heated to a temperature of, for example, 40° C. or higher and 100° C. or lower, as an example, 90° C. in the downstream-side circulation system 25*b*. As water is heated to a temperature of 40° C. or higher, the water-soluble flavor remaining in the downstream-side circulation system 25*b* can be efficiently removed as in the case of the upstream-side circulation system 25*a*. The deodorizing effect can thus be enhanced. Further, as the temperature of water is set to 100° C. or lower, the surge tank 4 or the like can be handled as a Class-2 pressure vessel instead of a Class-1 pressure vessel, and thus the deodorizing treatment step can be performed at low cost.

The time required to supply water to the downstream-side circulation system 25*b* may be 5 minutes or more and 60 minutes or less, and as an example, 10 minutes. As the time required to supply water to the downstream-side circulation system 25*b* is 5 minutes or more, the flavor remaining in the downstream-side circulation system 25*b* can be effectively removed. Further, as the time required to supply water to the downstream-side circulation system 25*b* is 60 minutes or less, downtime can be reduced and energy saving can be achieved.

(Third Rinsing Step)

Further, if necessary, water (third rinse water for a second circulation system) may be supplied to the downstream-side circulation system 25*b* after the second rinsing step in the downstream-side circulation system 25*b* described above. At this time, water is supplied to the downstream-side circulation system 25*b* as in the first rinsing step and the second rinsing step in the downstream-side circulation system 25*b* described above. In this case, water is heated to a temperature of, for example, 40° C. or higher and 100° C. or lower, as an example, 40° C. in the downstream-side circulation system 25*b*. As water is heated to a temperature of 40° C. or higher, the water-soluble flavor remaining in the downstream-side circulation system 25*b* can be removed more efficiently and the deodorizing effect can be enhanced. Further, as the temperature of water is set to 100° C. or lower, energy saving can be achieved.

Further, the time required to supply water to the downstream-side circulation system 25*b* may be 5 minutes or more and 120 minutes or less and as an example, 10 minutes. As the time required to supply water to the downstream-side circulation system 25*b* is 5 minutes or more, the flavor remaining in the downstream-side circulation system 25*b* can be removed more effectively and the deodorizing effect can be enhanced. Further, as the time required to supply water to the downstream-side circulation system 25*b* is 120 minutes or less, downtime can be reduced and energy saving can be achieved.

In this way, CIP is performed in the downstream-side circulation system 25*b*, the flavor remaining in the downstream-side circulation system 25*b* is removed by CIP, and the downstream-side circulation system 25*b* is deodorized.

(Deodorization Check Step)

A deodorization check step may be performed to determine whether or not the deodorizing effect is sufficient. At this deodorization check step, water is first sent to the filling system 100. At this time, water is sent in a state where the temperature at an outlet of the UHT 3 is reduced from the temperature at the time of the second rinsing step in the upstream-side circulation system 25*a* (for example, 140° C.) to about 80° C. or higher and 90° C. or lower. The deodorization check step can be performed by sampling water from the drain pipe 27*b* at an outlet of the filling device 6 and checking whether or not a scent is removed. At this time, a sensor capable of distinguishing scents may be provided. Alternatively, water may be filled in a vessel using the filling device 6 to check the scent. If the result of this deodorization check step is NG, CIP is performed again. The deodorization check step may be performed individually in the upstream-side circulation system 25*a* and the downstream-side circulation system 25*b*.

As described above, according to the present embodiment, the chemical is heated to a temperature of 70° C. or higher in the upstream-side circulation system 25*a* at the chemical circulation step in the upstream-side circulation system 25*a*. As a result, the flavor remaining in the upstream-side circulation system 25*a* can be efficiently removed. The temperature of the chemical is 150° C. or lower in the upstream-side circulation system 25*a*. Consequently, energy saving can be achieved. The fact that the flavor remaining in the upstream-side circulation system 25*a* can be efficiently removed will be described in a later embodiment.

Further, according to the present embodiment, the time required to supply and circulate the chemical in the upstream-side circulation system 25*a* or the downstream-side circulation system 25*b* is 5 minutes or more at the chemical circulation step. As a result, the flavor remaining in the upstream-side circulation system 25*a* or the downstream-side circulation system 25*b* can be effectively removed. Further, the time required to supply and circulate the chemical in the upstream-side circulation system 25*a* or the downstream-side circulation system 25*b* is 60 minutes or less. Consequently, downtime can be reduced and energy saving can be achieved.

Further, according to the present embodiment, water is heated to a temperature of 70° C. or higher in the upstream-side circulation system 25a at the second rinsing step. Water is heated to a temperature of 40° C. or higher in the downstream-side circulation system 25b. As a result, the water-soluble flavor remaining in the upstream-side circulation system 25a or the downstream-side circulation system 25b can be efficiently removed. The temperature of water is 150° C. or lower in the upstream-side circulation system 25a. The temperature of water is 100° C. or lower in the downstream-side circulation system 25b. Consequently, energy saving can be achieved. The fact that the water-soluble flavor remaining in the upstream-side circulation system 25a can be efficiently removed will be described in a later embodiment.

Further, according to the present embodiment, the time required to supply water to the upstream-side circulation system 25a or the downstream-side circulation system 25b is 5 minutes or more at the second rinsing step. As a result, the flavor remaining in the upstream-side circulation system 25a or the downstream-side circulation system 25b can be effectively removed. Further, the time required to supply water to the upstream-side circulation system 25a or the downstream-side circulation system 25b is 60 minutes or less. Consequently, downtime can be reduced and energy saving can be achieved.

The above embodiment has described an example in which the chemical is heated to a temperature of 70° C. or higher and 100° C. or lower at the chemical circulation step in the downstream-side circulation system 25b, but the present invention is not limited thereto. That is, the above embodiment has described the example in which the chemical is heated to a temperature of 70° C. or higher and 100° C. or lower assuming that the surge tank 4 or the like in the downstream-side circulation system 25b is treated as a Class-2 pressure vessel. On the other hand, when the surge tank 4 or the like in the downstream-side circulation system 25b is handled as a Class-1 pressure vessel, the chemical may be heated to a temperature of, for example, 70° C. or higher and 150° C. or lower, as an example, 130° C. at the chemical circulation step in the downstream-side circulation system 25b. Also in this case, as the chemical is heated to a temperature of 70° C. or higher, the flavor remaining in the downstream-side circulation system 25b can be efficiently removed. As the temperature of the chemical is set to a temperature of 150° C. or lower, energy saving can be achieved. As the chemical is heated to a high temperature of, as an example, 130° C., the flavor remaining in the downstream-side circulation system 25b can be removed more efficiently.

The above embodiment has described an example in which the filling system 100 includes the manifold valve 21, but the present invention is not limited thereto. For example, CIP may be performed at the same time from the UHT 3 to the filling device 6 without providing the manifold valve 21.

Figure 6:
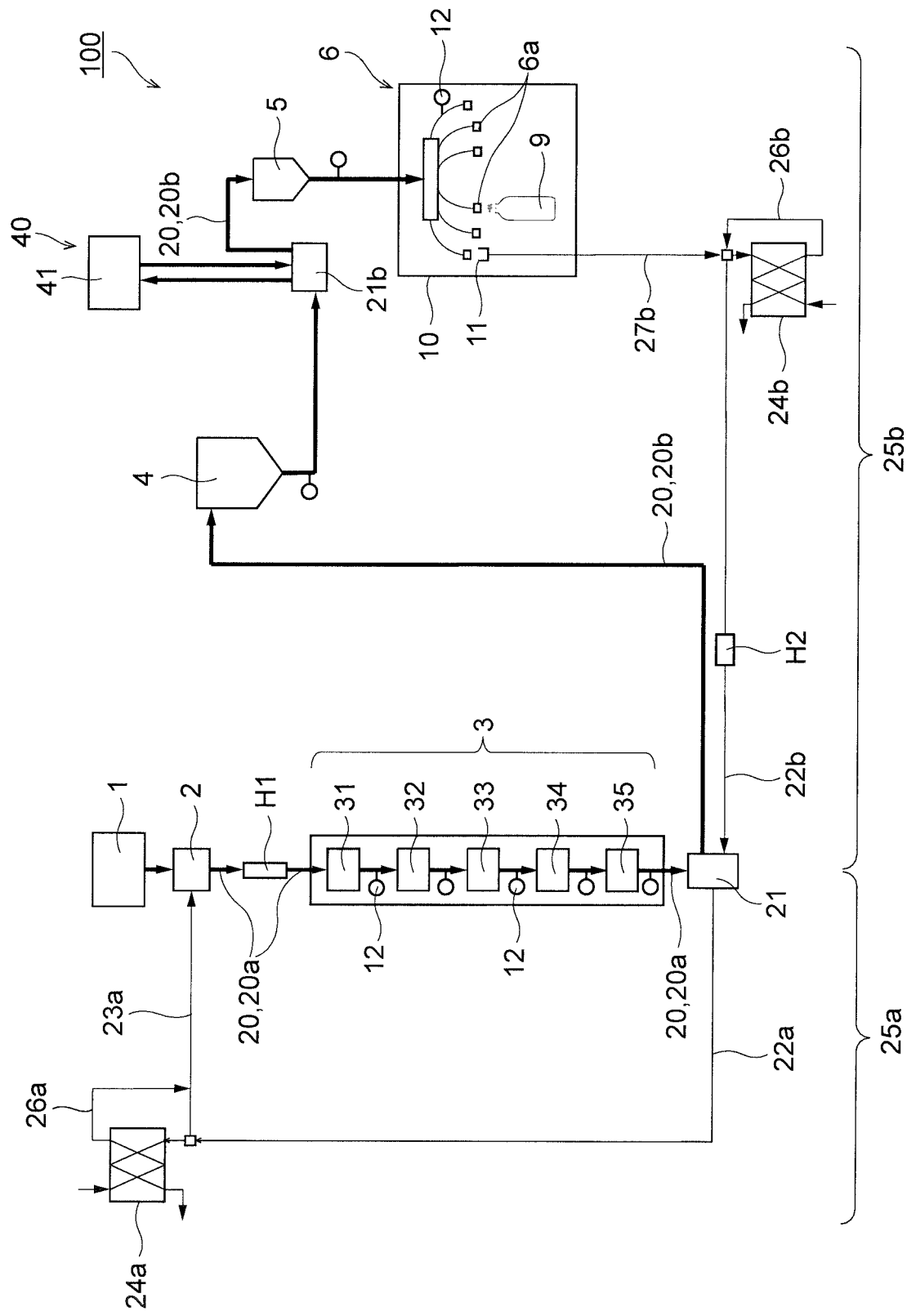
FIG. 6 is a block diagram illustrating a modification of the filling system to which the deodorizing method according to the first embodiment of the present invention is applied.

Further, as illustrated in FIG. 6, the filling system 100 may further include a carbonic acid line 40 having a carbonic acid adding device 41 that adds carbonic acid to a drink. In this case, the carbonic acid line 40 is connected to the downstream-side supply pipe 20b via a manifold valve 21b provided between the surge tank 4 and the surge tank for filler 5. As a result, as indicated by thick lines in FIG. 6, the drink is supplied to the carbonic acid line 40 through the downstream-side supply pipe 20b, and carbonic acid is added by the carbonic acid adding device 41. The drink having carbonic acid added thereto is supplied from the carbonic acid line 40 through the manifold valve 21b to the downstream-side supply pipe 20b and the surge tank for filler 5, and is filled in the vessel 9 by the filling device 6.

When only the surge tank for filler 5 is disposed in and the surge tank 4 is not disposed in the filling system 100, the manifold valve 21b described above may be provided on the downstream side of the surge tank for filler 5.

In CIP, the heating device for heating water may be, for example, an aseptic water sterilizer used in an aseptic filling machine for bottle rinse, cap rinse, or the like, or may be another product heating sterilizer.

Further, the UHT 3 may be an injection type or an infusion type, and the heat exchanger used for performing heat exchange in the filling system 100, such as the heat exchanger of the UHT 3, may be a plate type heat exchanger or a shell and tube type heat exchanger.

Second Embodiment

Figure 7:
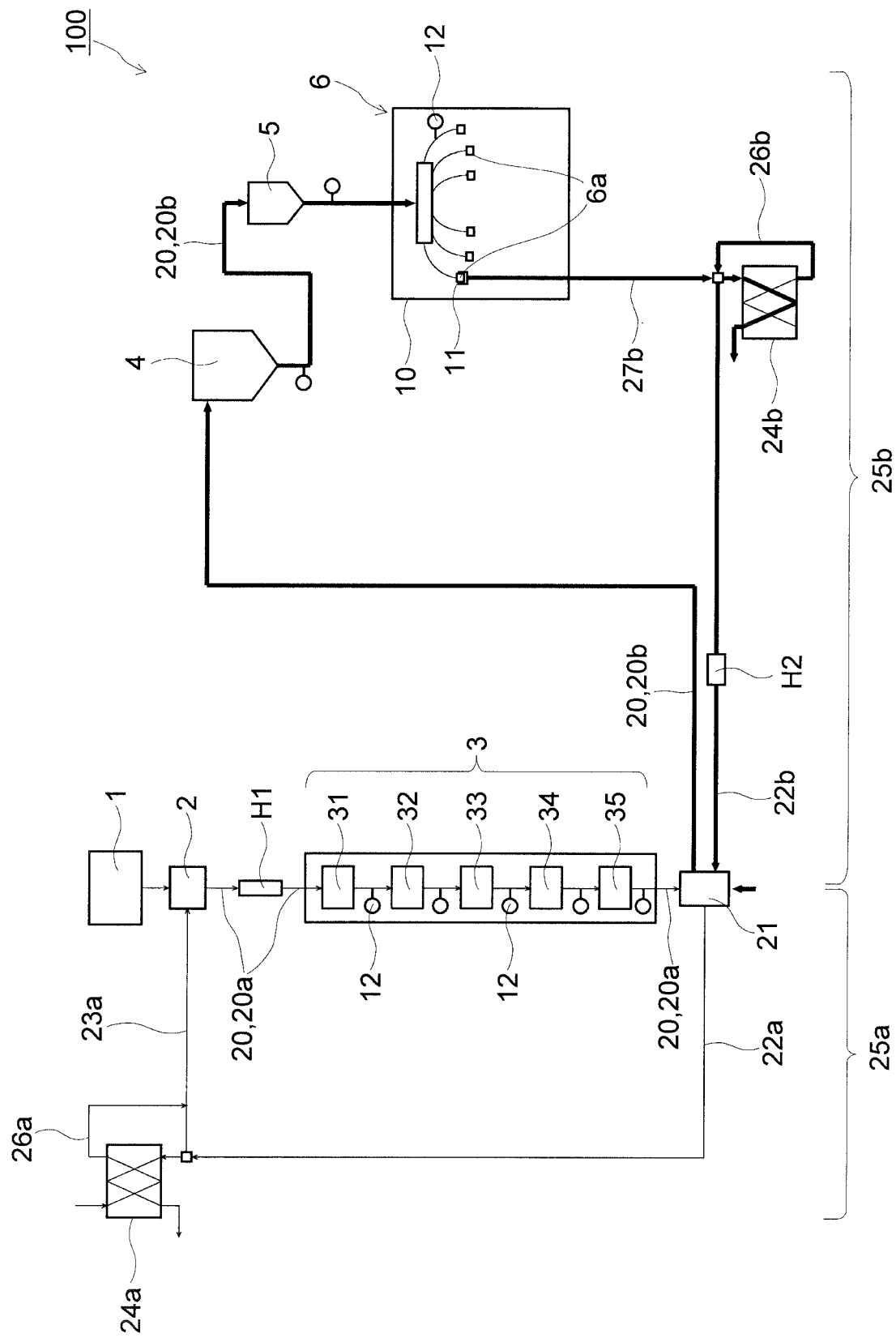
FIG. 7 is a block diagram illustrating a deodorizing method according to a second embodiment of the present invention.
Figure 8:
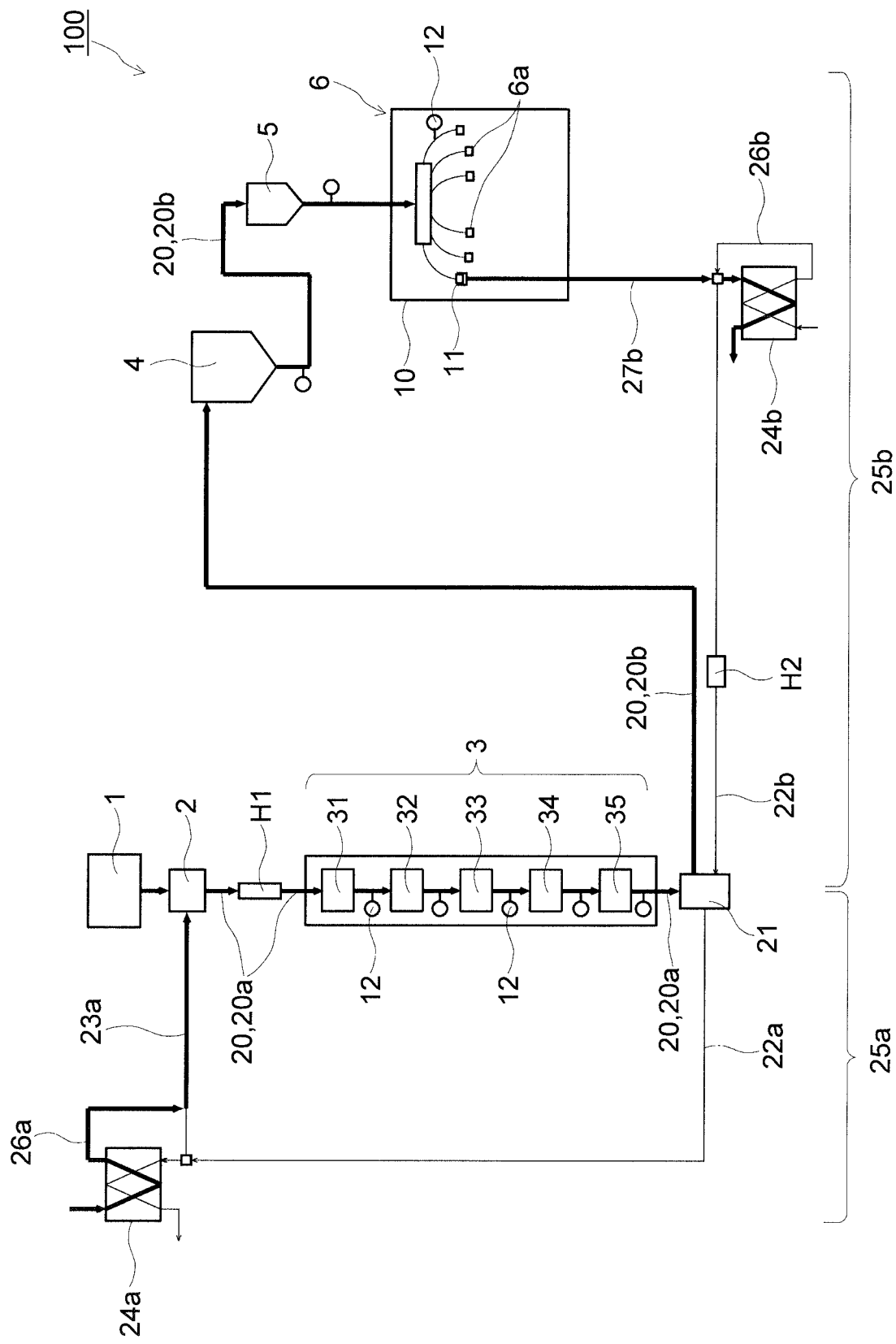
FIG. 8 is a block diagram illustrating the deodorizing method according to the second embodiment of the present invention.

Next, a deodorizing method according to a second embodiment of the present invention will be described with reference to FIG. 2 to FIG. 5, FIG. 7, and FIG. 8. In FIG. 7 and FIG. 8, the same reference numerals are given to the same portions as those of the first embodiment, and detailed description thereof will be omitted. In FIG. 7 to FIG. 8, pipes through which water, a chemical, and steam pass are indicated by thick lines. Further, when the deodorizing method according to the present embodiment is described with reference to FIG. 2 to FIG. 5 referred to in the first embodiment described above, the pipes indicated by the thick lines may pass steam.

First, after drink filling in the filling system 100 is completed, an operation button of a control device (not illustrated) is operated. As will be described later, CIP and SIP are performed in a predetermined procedure in the upstream-side circulation system 25a and the downstream-side circulation system 25b (see FIG. 2 to FIG. 5). At this time, the manifold valve 21 is switched, so that the upstream-side supply pipe 20a communicates with the upstream-side return pipe 22a (see FIG. 2 and FIG. 3), and the downstream-side supply pipe 20b communicates with the downstream-side return pipe 22b (see FIG. 4 and FIG. 5). CIP and SIP of the upstream-side circulation system 25a and CIP and SIP of the downstream-side circulation system 25b may be performed in sequence or in parallel with each other. A CIP step (first CIP step) and an SIP step (first SIP step) of the upstream-side circulation system 25a will be described first.

(CIP Step)
(First Rinsing Step)

As illustrated in FIG. 2, water is supplied first to the upstream-side circulation system 25a. At this time, water is supplied first from the upstream-side supply mechanism 24a to the balance tank 2 through the upstream-side introduction pipe 26a. At this time, water is supplied to the upstream-side circulation system 25a at a temperature of, for example, 10° C. or higher and 40° C. or lower, as an example, 15° C. At this time, water may be supplied to the balance tank 2 from a pipe or the like (not illustrated) without using the upstream-side supply mechanism 24a.

Next, the water supplied to the upstream-side circulation system 25a flows in the upstream-side supply pipe 20a to pass through the manifold valve 21. The water is then supplied to the upstream-side return pipe 22a, passes through the upstream-side return pipe 22a, and is discharged as a waste solution from the upstream-side supply mechanism 24a to the outside. At this time, in the upstream-side supply mechanism 24a, heat exchange may be performed between water to be supplied and water to be discharged to the outside.

When water is supplied to the upstream-side circulation system 25a as described above, the time required to supply water to the upstream-side circulation system 25a may be 5 minutes or more and 30 minutes or less, as an example, 5 minutes.

(Chemical Circulation Step)

Next, as illustrated in FIG. 3, a chemical is supplied and circulated in the upstream-side circulation system 25a. At this time, the chemical is supplied first from the upstream-side supply mechanism 24a to the balance tank 2 through the upstream-side introduction pipe 26a. In this case, an alkaline cleaning solution containing sodium hydroxide or potassium hydroxide in an amount of 0.1 to 10% by mass or an alkaline cleaning solution containing sodium hypochlorite having a chlorine concentration of 100 to 3,000 ppm may be used as the chemical. At this time, the chemical may be supplied to the balance tank 2 or the heater H1 from a pipe or the like (not illustrated) without using the upstream-side supply mechanism 24a.

The chemical supplied to the balance tank 2 passes through the balance tank 2 and is heated by the heater H1 disposed on the downstream side of the balance tank 2. The chemical heated by the heater H1 is sent to the UHT 3 through the upstream-side supply pipe 20a and further heated by the UHT 3. At this time, the chemical is heated to a temperature of, for example, 70° C. or higher and 150° C. or lower, as an example, 80° C.

Next, the heated chemical flows in the upstream-side supply pipe 20a to pass through the UHT 3 and the manifold valve 21. The heated chemical is supplied to the upstream-side return pipe 22a and then is supplied to the bypass pipe 23a connected to the upstream-side return pipe 22a. The chemical is then supplied into the balance tank 2 through the bypass pipe 23a. In this way, the chemical circulates in the upstream-side circulation system 25a. The chemical may be supplied to the heater H1 through the bypass pipe 23a by a pipe (not illustrated) or the like to circulate in the upstream-side circulation system 25a. The chemical circulates in the upstream-side circulation system 25a for a predetermined period of time, and then is discharged as a waste solution from the upstream-side supply mechanism 24a to the outside (see FIG. 2). In this case, the time required to supply and circulate the chemical in the upstream-side circulation system 25a may be 5 minutes or more and 60 minutes or less, and as an example, 15 minutes.

If necessary, cleaning with an acidic cleaning solution may be performed before and after cleaning with an alkaline cleaning solution. Further, for example, the cleaning with the acidic cleaning solution may be performed first, followed by the cleaning with the alkaline cleaning solution, and then the cleaning with the acidic cleaning solution may be performed. Alternatively, the cleaning with the alkaline cleaning solution may be performed first, followed by the cleaning with the acidic cleaning solution, and then the cleaning with the alkaline cleaning solution may be performed.

(Second Rinsing Step)

Next, as illustrated in FIG. 2, water is supplied to the upstream-side circulation system 25a. At this time, water is supplied to the upstream-side circulation system 25a as in the first rinsing step described above. In this case, water is supplied to the upstream-side circulation system 25a at a temperature of, for example, 10° C. or higher and 40° C. or lower, as an example, 15° C. The time required to supply water to the upstream-side circulation system 25a may be 5 minutes or more and 60 minutes or less, and as an example, 10 minutes. Also in this time, water may be supplied to the balance tank 2 from a pipe or the like (not illustrated) without using the upstream-side supply mechanism 24a.

(Third Rinsing Step)

Further, if necessary, water may be supplied to the upstream-side circulation system 25a after the second rinsing step described above. At this time, water is supplied to the upstream-side circulation system 25a as in the first rinsing step and the second rinsing step described above. In this case, in the upstream-side circulation system 25a, water is supplied to the upstream-side circulation system 25a at a temperature of, for example, 10° C. or higher and 40° C. or lower, as an example, 15° C. The time required to supply water to the upstream-side circulation system 25a may be 5 minutes or more and 60 minutes or less, and as an example, 10 minutes. Also in this time, water may be supplied to the balance tank 2 from a pipe or the like (not illustrated) without using the upstream-side supply mechanism 24a.

In this way, CIP of the upstream-side circulation system 25a is performed.

After CIP of the upstream-side circulation system 25a is performed, SIP of the upstream-side circulation system 25a is performed.

(SIP Step)

As illustrated in FIG. 3, water is supplied and circulated first in the upstream-side circulation system 25a. At this time, water is supplied first from the upstream-side supply mechanism 24a to the balance tank 2 through the upstream-side introduction pipe 26a. The water supplied to the balance tank 2 is sent to the UHT 3 through the upstream-side supply pipe 20a, and is heated and sterilized by the UHT 3. At this time, the water is heated to a temperature of, for example, 90° C. or higher and 150° C. or lower, as an example, 95° C. At this time, water may be supplied to the balance tank 2 or the heater H1 from a pipe or the like (not illustrated) without using the upstream-side supply mechanism 24a.

Next, the water heated by the UHT 3 flows in the upstream-side supply pipe 20a to pass through the manifold valve 21. The heated water is supplied to the upstream-side return pipe 22a and then is supplied to the bypass pipe 23a connected to the upstream-side return pipe 22a. The water is then supplied into the balance tank 2 through the bypass pipe 23a. In this way, water circulates in the upstream-side circulation system 25a. Water may be supplied to the heater H1 through the bypass pipe 23a by a pipe (not illustrated) or the like to circulate in the upstream-side circulation system 25a. Water circulates in the upstream-side circulation system 25a for a predetermined period of time, and then is discharged as a waste solution from the upstream-side supply mechanism 24a to the outside (see FIG. 2).

When water is supplied and circulated in the upstream-side circulation system 25a as described above, the time required to supply and circulate water in the upstream-side circulation system 25a may be 5 minutes or more and 60 minutes or less, as an example, 5 minutes.

Instead of water, a sterilizing working fluid such as steam or the chemical described above may be supplied to the upstream-side circulation system 25a.

In this way, SIP of the upstream-side circulation system 25a is performed.

The UHT 3 or the like heated for SIP is then cooled to a desired set temperature while an aseptic state is maintained.

Next, a CIP step (second CIP step) and an SIP step (second SIP step) of the downstream-side circulation system 25b will be described.

(CIP Step)

As illustrated in FIG. 4, the cup 11 is first put on the filling nozzle 6a. The drain pipe 27b is thus connected to the filling nozzle 6a.

(First Rinsing Step)

Next, water is supplied to the downstream-side circulation system 25b. At this time, water is supplied first from the downstream-side supply mechanism 24b to the downstream-side return pipe 22b through the downstream-side introduction pipe 26b. At this time, water is supplied to the downstream-side circulation system 25b at a temperature of, for example, 5° C. or higher and 40° C. or lower, as an example, 15° C.

Next, the supplied water flows in the downstream-side return pipe 22b to pass through the manifold valve 21. At this time, the water is supplied to the downstream-side supply pipe 20b, passes through the downstream-side supply pipe 20b, the surge tank 4, the surge tank for filler 5, the filling device 6, and the drain pipe 27b, and is discharged as a waste solution from the downstream-side supply mechanism 24b to the outside.

When water is supplied to the downstream-side circulation system 25b as described above, the time required to supply water to the downstream-side circulation system 25b may be 5 minutes or more and 30 minutes or less, as an example, 5 minutes.

(Chemical Circulation Step)

Next, as illustrated in FIG. 5, a chemical is supplied and circulated in the downstream-side circulation system 25b. At this time, the chemical is supplied first from the downstream-side supply mechanism 24b to the downstream-side return pipe 22b through the downstream-side introduction pipe 26b. The alkaline cleaning solution similar to the chemical used when CIP is performed in the upstream-side circulation system 25a can be used as the chemical. The chemical supplied to the downstream-side return pipe 22b is heated by the heater H2. At this time, the chemical is heated to a temperature of, for example, 70° C. or higher and 150° C. or lower, as an example, 80° C.

Next, the heated chemical passes through the manifold valve 21, and then passes through the downstream-side supply pipe 20b, the surge tank 4, the surge tank for filler 5, and the filling device 6. The chemical is then supplied to the downstream-side return pipe 22b through the drain pipe 27b. In this way, the chemical circulates in the downstream-side circulation system 25b. The chemical circulates in the downstream-side circulation system 25b for a predetermined period of time, and then is discharged as a waste solution from the downstream-side supply mechanism 24b to the outside (see FIG. 4). In this case, the time required to supply and circulate the chemical in the downstream-side circulation system 25b may be 5 minutes or more and 60 minutes or less, and as an example, 15 minutes.

If necessary, cleaning with an acidic cleaning solution may be performed before and after cleaning with an alkaline cleaning solution, as in the upstream-side circulation system 25a. Further, for example, the cleaning with the acidic cleaning solution may be performed first, followed by the cleaning with the alkaline cleaning solution, and then the cleaning with the acidic cleaning solution may be performed. Alternatively, the cleaning with the alkaline cleaning solution may be performed first, followed by the cleaning with the acidic cleaning solution, and then the cleaning with the alkaline cleaning solution may be performed.

(Second Rinsing Step)

Next, as illustrated in FIG. 4, water is supplied to the downstream-side circulation system 25b. At this time, water is supplied to the downstream-side circulation system 25b as in the first rinsing step in the downstream-side circulation system 25b described above. In this case, in the downstream-side circulation system 25b, water is supplied to the downstream-side circulation system 25b at a temperature of, for example, 10° C. or higher and 40° C. or lower, as an example, 15° C. Further, the time required to supply water to the downstream-side circulation system 25b may be 5 minutes or more and 60 minutes or less, and as an example, 10 minutes.

(Third Rinsing Step)

Further, if necessary, water may be supplied to the downstream-side circulation system 25b after the second rinsing step in the downstream-side circulation system 25b described above. At this time, water is supplied to the downstream-side circulation system 25b as in the first rinsing step and the second rinsing step in the downstream-side circulation system 25b described above. In this case, in the downstream-side circulation system 25b, water is supplied to the downstream-side circulation system 25b at a temperature of, for example, 10° C. or higher and 40° C. or lower, as an example, 15° C. Further, the time required to supply water to the downstream-side circulation system 25b may be 5 minutes or more and 120 minutes or less, and as an example, 10 minutes.

In this way, CIP of the downstream-side circulation system 25b is performed.

After CIP of the downstream-side circulation system 25b is performed, SIP of the downstream-side circulation system 25b is performed.

(SIP Step)

First, as illustrated in FIG. 7, steam is supplied to the downstream-side circulation system 25b. At this time, steam is supplied first from the manifold valve 21. At this time, steam is supplied to the downstream-side circulation system 25b at a temperature of, for example, 90° C. or higher and 150° C. or lower, as an example, 135° C. Steam may be supplied from the top of the tanks 4 and 5.

Next, the steam supplied to the manifold valve 21 passes through the downstream-side supply pipe 20b, the surge tank 4, the surge tank for filler 5, the filling device 6, and the drain pipe 27b to be discharged to the outside.

When steam is supplied to the downstream-side circulation system 25b as described above, the time required to supply steam to the downstream-side circulation system 25b may be 5 minutes or more and 60 minutes or less, as an example, 5 minutes.

Instead of steam, a sterilizing working fluid such as water or the chemical used for CIP cleaning and described above may be supplied to the downstream-side circulation system 25b.

In this way, SIP of the downstream-side circulation system 25b is performed.

The downstream-side circulation system 25b is then cooled with aseptic air. At this time, aseptic air flows into the downstream-side supply pipe 20b to cool the downstream-side supply pipe 20b, the surge tank 4, the filling device 6, and the like. At this time, for example, cooling with aseptic air is performed until the temperature of a flow path in the filling device 6, through which a content passes, is 60° C. or higher and 100° C. or lower. After that, the downstream-side circulation system 25b may be cooled by supplying aseptic water to the downstream-side circulation system 25b.

(Deodorizing Treatment Step)

Next, a deodorizing treatment step of performing a deodorizing process on the upstream-side circulation system 25a and the downstream-side circulation system 25b will be described.

After SIP of the upstream-side circulation system 25a and the downstream-side circulation system 25b is completed, an operation button of a control device (not illustrated) is operated first. The manifold valve 21 is thus switched, so that the upstream-side supply pipe 20a and the downstream-side supply pipe 20b communicate with each other (see FIG. 8).

Next, water is supplied to the upstream-side circulation system 25a having been subjected to SIP. At this time, water is supplied from the upstream-side supply mechanism 24a to the balance tank 2 through the upstream-side introduction pipe 26a, as illustrated in FIG. 8. The water supplied to the balance tank 2 is sent to the UHT 3 through the upstream-side supply pipe 20a. Also in this time, water may be supplied to the balance tank 2 from a pipe or the like (not illustrated) without using the upstream-side supply mechanism 24a.

Next, the water supplied to the upstream-side circulation system 25a is heated by the UHT 3 to be sterilized. As the supplied water is heated by the UHT 3 to be sterilized, the deodorizing process can be performed in the filling system 100 while an aseptic state is maintained. At this time, water is sterilized under conditions that a heat load having a sterilization value equal to or more than that in conditions for sterilizing the product to to be produced next is applied, and then is heated so that the temperature at the outlet of the UHT 3 is, for example, 70° C. or higher and 100° C. or lower, as an example, 90° C. As water is heated to a temperature of 90° C. or higher, the flavor, particularly the water-soluble flavor, remaining in the upstream-side circulation system 25a can be efficiently removed. The deodorizing effect can thus be enhanced. Further, as the temperature of water is set to 90° C. or lower, each of the tanks 4 and 5 can be handled as a Class-2 pressure vessel instead of a Class-1 pressure vessel, and thus the deodorizing treatment step can be performed at low cost. In order to enhance the deodorizing effect, each of the tanks 4 and 5 may be changed to a Class-1 pressure vessel to perform deodorization with water at 100° C. or higher, though it incurs costs. In this case, when water is discharged to the outside of the circulation systems 25a and 25b, the temperature of the water may be reduced to lower than 100° C. before discharging.

The time required to supply water to the upstream-side circulation system 25a may be 5 minutes or more and 120 minutes or less, and as an example, 30 minutes. As the time required to supply water to the upstream-side circulation system 25a is 5 minutes or more, the flavor remaining in the upstream-side circulation system 25a can be effectively removed. Further, as the time required to supply water to the upstream-side circulation system 25a is 120 minutes or less, downtime can be reduced and energy saving can be achieved.

Next, the water heated by UHT 3 is supplied to the downstream-side circulation system 25b having been subjected to SIP. At this time, the water heated by the UHT 3 flows in the upstream-side supply pipe 20a to pass through the manifold valve 21. The water is then supplied to the downstream-side supply pipe 20b.

Next, the water supplied to the downstream-side supply pipe 20b flows in the surge tank 4, the surge tank for filler 5, the filling device 6, and the drain pipe 27b, and is discharged as a waste solution from the downstream-side supply mechanism 24b to the outside. At this time, the drain pipe 27b may be removed from the filling nozzle 6a, and the water is discharged into the aseptic chamber 10. In this case, the water is discharged as a waste solution from a drain pipe (not illustrated) connected to the aseptic chamber 10 to the outside.

As described above, when the water heated by UHT 3 is supplied to the downstream-side circulation system 25b, the time required to supply water to the downstream-side circulation system 25b may be 5 minutes or more and 120 minutes or less, and as an example, 30 minutes. As the time required to supply water to the downstream-side circulation system 25b is 5 minutes or more, the flavor remaining in the downstream-side circulation system 25b can be effectively removed. Further, as the time required to supply water to the downstream-side circulation system 25b is 120 minutes or less, downtime can be reduced and energy saving can be achieved.

(Deodorization Check Step)

A deodorization check step may be performed to determine whether or not the deodorizing effect is sufficient. At this deodorization check step, water is first sent to the filling system 100. At this time, water is sent in a state where the temperature at the outlet of the UHT 3 is reduced from the temperature during the deodorizing treatment step (for example, 90° C.) to about 30° C. or higher and 40° C. or lower. The deodorization check step can be performed by sampling water from the drain pipe 27b at the outlet of the filling device 6 and checking whether or not a scent is removed. At this time, a sensor capable of distinguishing scents may be provided. Alternatively, water may be filled in a vessel using the filling device 6 to check the scent. If the result of this deodorization check step is NG, the deodorizing treatment step is performed again.

Meanwhile, the preparation device 1 prepares, for example, a fruit drink or the like as a drink, as described above. Such drinks include drinks containing many flavors. At this time, if a flavor remains in the upstream-side circulation system 25a and the downstream-side circulation system 25b, the remaining flavor may be mixed with the next drink and the scent of the previous drink may be attached to the next drink.

In particular, for example, fluororesin packing is provided as a sealing member at connection points of pipes, members, or the like in the upstream-side circulation system 25a, as described above. In addition, for example, packing made of ethylene propylene diene rubber (EPDM) is provided as a sealing member at connection points of pipes, members, or the like in the downstream-side circulation system 25b, as described above. Further, when a drink is filled in the vessel 9 (see FIG. 1), the drink is heated by the UHT 3 to a temperature of about 60° C. or higher and 150° C. or lower, as described above. At this time, the packing provided at the connection points of the pipes may thermally expand, resulting in a gap between each pipe and the packing. If a gap is formed between each pipe and the packing, the flavor may enter the gap. In this case, when the packing is cooled to contract, the flavor having entered the gap may be present between each pipe and the packing in a state of adhering to the packing. Further, it may be difficult to remove the flavor present between each pipe and the packing even if water is supplied or a chemical is circulated in the upstream-side circulation system 25a and the downstream-side circulation system 25b. Then, the flavor having entered such a gap may enter the next drink through the gap between each pipe and the packing, the gap resulting from the thermal expansion of the packing during the filling of the next drink.

According to the present embodiment, water is heated to a temperature of 60° C. or higher and 150° C. or lower at the deodorizing treatment step, the flavor remaining in the upstream-side circulation system 25a and the downstream-side circulation system 25b can be efficiently removed. That is, as water is heated to a temperature of 60° C. or higher and 150° C. or lower, the amount of thermal expansion of the packing can be close to the amount of thermal expansion of the packing when a drink is filled. This makes it possible to effectively remove the flavor having entered the gap due to the thermal expansion of the packing. It is thus possible to prevent the scent of the previous drink from being attached to the next drink. In particular, packing made of ethylene propylene diene rubber (EPDM) may be used in the downstream-side circulation system 25b. Flavors tend to adhere to ethylene propylene diene rubber, and flavors tend to remain in the downstream-side circulation system 25b. The flavor adhering to the packing can be effectively removed by heating water to a temperature of 60° C. or higher and 150° C. or lower. In this case, in order to achieve a higher deodorizing effect, it is effective to perform rinsing with water at a temperature higher than or equal to the sterilization temperature of the previous product. The flavors described above include water-soluble flavors such as ethyl butyrate and ethyl 2-methylbutyrate. In this case, as water is heated to a temperature of 60° C. or higher and 150° C. or lower, the water-soluble flavor remaining in the upstream-side circulation system 25a and the downstream-side circulation system 25b can be efficiently removed. The deodorizing effect can thus be enhanced.

As described above, according to the present embodiment, the deodorizing treatment step includes a step of supplying water to the upstream-side circulation system 25a having been subjected to SIP, a step of heating the water supplied to the upstream-side circulation system 25a by the UHT 3, and a step of supplying the water heated by the UHT 3 to the downstream-side circulation system 25b having been subjected to SIP. As described above, by supplying water to the upstream-side circulation system 25a having been subjected to an SIP treatment and heating the water, and supplying the heated water to the downstream-side circulation system 25b, the flavor remaining in the upstream-side circulation system 25a and the downstream-side circulation system 25b can be removed while an aseptic state is maintained.

Further, according to the present embodiment, water is heated to a temperature of 70° C. or higher at the deodorizing treatment step. The flavor, particularly the water-soluble flavor, remaining in the upstream-side circulation system 25a and the downstream-side circulation system 25b can be efficiently removed. The temperature of water is 100° C. or lower. Consequently, energy saving and cost reduction can be achieved.

Further, according to the present embodiment, the time required to supply water to the upstream-side circulation system 25a is 5 minutes or more at the deodorizing treatment step. As a result, the flavor remaining in the upstream-side circulation system 25a can be effectively removed. Further, the time required to supply water to the upstream-side circulation system 25a is 120 minutes or less. Consequently, downtime can be reduced and energy saving can be achieved.

Further, according to the present embodiment, the time required to supply the water heated by the UHT 3 to the downstream-side circulation system 25b is 5 minutes or more at the deodorizing treatment step. As a result, the flavor remaining in the downstream-side circulation system 25b can be effectively removed. Further, the time required to supply water to the downstream-side circulation system 25b is 120 minutes or less. Consequently, downtime can be reduced and energy saving can be achieved.

The above embodiment has described an example in which after SIP of the downstream-side circulation system 25b is performed, cooling is performed with aseptic air until the temperature of the flow path in the filling device 6, through which a content passes, is 60° C. or higher and 100° C. or lower, but the present invention is not limited thereto. For example, after the temperature of the flow path in the filling device 6, through which a content passes, in the downstream-side circulation system 25b is cooled with aseptic air to a temperature of 80° C. or higher and 100° C. or lower, the water heated by the UHT 3 is preferably supplied from the upstream-side circulation system 25a to the downstream-side circulation system 25b. As the temperature of the filling device 6 after cooling with aseptic air is 80° C. or higher in the downstream-side circulation system 25b, the water heated by the UHT 3 (70° C. or higher and 100° C. or lower) can be supplied from the upstream-side circulation system 25a to the downstream-side circulation system 25b while the packing in the downstream-side circulation system 25b thermally expands. Consequently, the flavor having entered a gap formed when the packing thermally expands can be effectively removed, and it is possible to prevent the scent of the previous drink from being attached to the next drink.

Also, the above embodiment has described an example in which the filling system 100 includes the manifold valve 21, but the present invention is not limited thereto. For example, CIP and SIP may be performed at the same time from the UHT 3 to the filling device 6 without providing the manifold valve 21.

Further, the above embodiment has described an example in which SIP is performed after CIP in the upstream-side circulation system 25a and the downstream-side circulation system 25b, but the present invention is not limited thereto. For example, as the chemical is heated to a temperature of 70° C. or higher, and supplied and circulated in the upstream-side circulation system 25a and the downstream-side circulation system 25b for 5 minutes or more at the chemical circulation step of CIP, the pipes and members in the upstream-side circulation system 25a and the downstream-side circulation system 25b may be sterilized. This makes it possible to omit SIP, which is usually performed after CIP. Downtime can thus be reduced.

Figure 9:
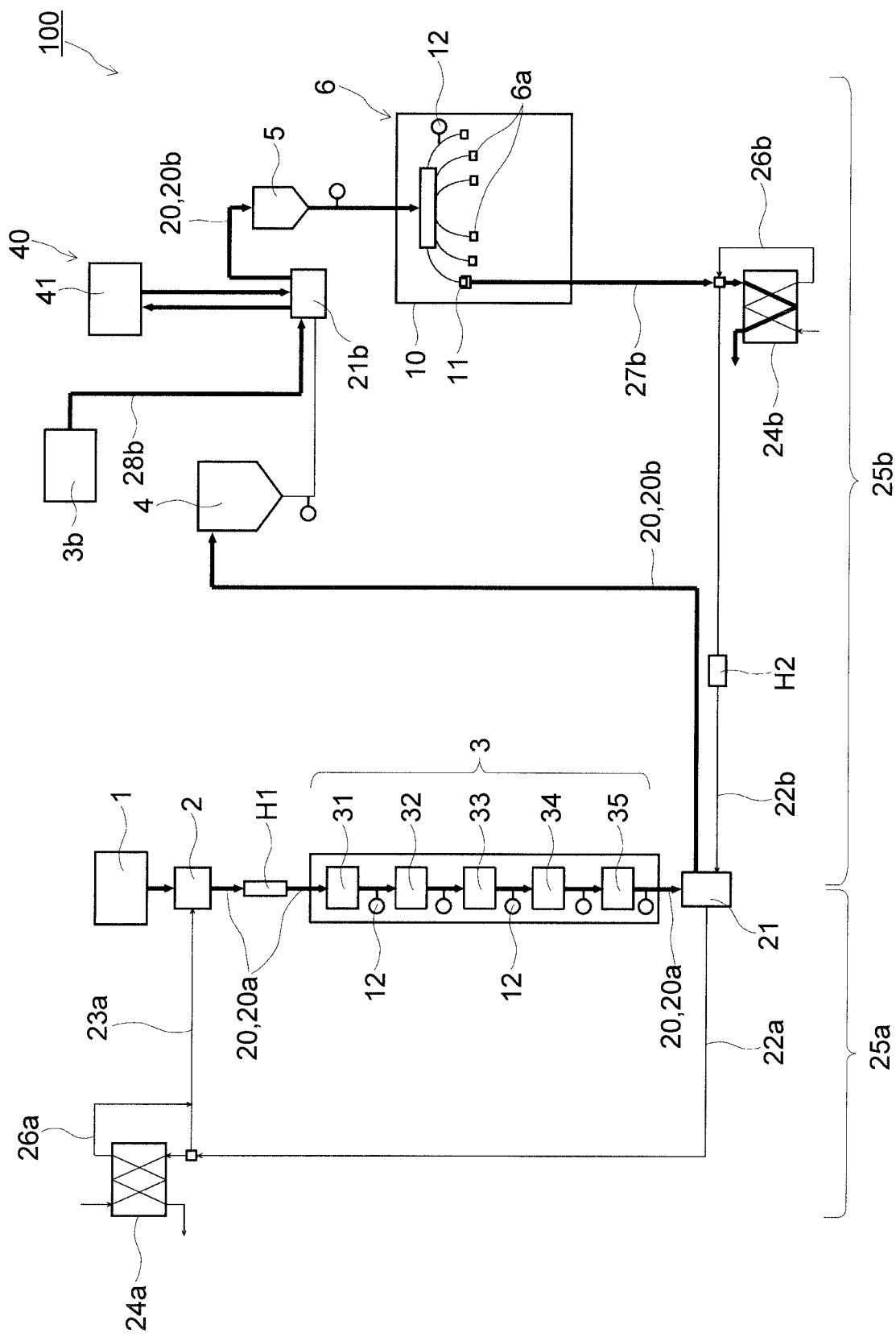
FIG. 9 is a block diagram illustrating a modification of the deodorizing method according to the second embodiment of the present invention.

The above embodiment has described an example in which water is heated by the UHT 3 at the deodorizing treatment step, but the present invention is not limited thereto. For example, as illustrated in FIG. 9, the downstream-side circulation system 25b may include a heat sterilizer (heat sterilizer for preparing aseptic water) (hereinafter, referred to as "UHT") 3b that is connected to the downstream side of the surge tank 4 and prepares aseptic water, and at the deodorizing treatment step, water may be supplied to the UHT 3b to be heated, and the water heated by the UHT 3b may be supplied to the downstream-side circulation system 25b having been subjected to SIP.

In this time, the water heated by the UHT 3b flows in an aseptic water supply pipe 28b to pass through a manifold valve 21b. The water circulates in the carbonic acid line 40, and then passes through the manifold valve 21b to be supplied to the downstream-side supply pipe 20b. The water heated by the UHT 3b may be directly sent to the filling device 6 without flowing in the carbonic acid line.

Next, the water supplied to the downstream-side supply pipe 20b flows in the surge tank for filler 5, the filling device 6, and the drain pipe 27b, and is discharged as a waste solution from the downstream-side supply mechanism 24b to the outside. At this time, the drain pipe 27b may be removed from the filling nozzle 6a, and the water is discharged into the aseptic chamber 10. In this case, the water is discharged as a waste solution from a drain pipe (not illustrated) connected to the aseptic chamber 10 to the outside.

At this time, water may be heated so that the temperature at an outlet of the UHT 3b is 70° C. or higher and 100° C. or less, as an example, 90° C. As water is heated to a temperature of 90° C. or higher, the flavor, particularly the water-soluble flavor, remaining in the downstream-side circulation system 25b can be efficiently removed. The deodorizing effect can thus be enhanced. Further, as the temperature of water is set to 90° C. or lower, the surge tank for filler 5 or the like can be handled as a Class-2 pressure vessel instead of a Class-1 pressure vessel, and thus the deodorizing treatment step can be performed at low cost.

Further, the time required to supply water to the downstream-side circulation system 25b may be 5 minutes or more and 120 minutes or less, and as an example, 30 minutes. As the time required to supply water to the downstream-side circulation system 25b is 5 minutes or more, the flavor remaining in the downstream-side circulation system 25b can be effectively removed. Further, as the time required to supply water to the downstream-side circulation system 25b is 120 minutes or less, downtime can be reduced and energy saving can be achieved.

As described above, according to the present modification, the downstream-side circulation system 25b includes the UHT 3b connected to the downstream side of the surge tank 4, and at the deodorizing treatment step, water is supplied to the UHT 3b to be heated, and the water heated by the UHT 3b is supplied to the downstream-side circulation system 25b having been subjected to SIP. Consequently, as indicated by thick lines in FIG. 9, while the deodorizing treatment step is performed in the downstream-side circulation system 25b, the next product can be prepared in the upstream-side circulation system 25a where SIP has finished, and the next product can also be stored in the surge tank 4. Downtime can thus be significantly reduced.

In the filling system 100, when one of the tanks 4 and 5 is not provided and only one surge tank for filler is provided, the manifold valve 21b described above is preferably provided on the downstream side of the surge tank for filler.

At the deodorizing treatment step, the heating device for heating water may be, for example, an aseptic water sterilizer used in an aseptic filling machine for bottle rinse, cap rinse, or the like, or may be another product heating sterilizer.

Further, the UHT 3b may be an injection type or an infusion type, similarly to the UHT 3.

EXAMPLES

Next, specific examples of the present invention will be described.

Example

First, a fruit drink was supplied to the upstream-side circulation system 25a of the filling system 100 having the configuration illustrated in FIG. 1, and was circulated in the upstream-side circulation system 25a for 4 hours.

At that time, the supply temperature of the fruit drink was 20° C., the temperature of the fruit drink heated by the holding tube 33 of the UHT 3 was 115° C., and the temperature of the fruit drink having passed through the second-stage cooling section 35 was 30° C.

Next, the fruit drink was discharged from the upstream-side supply mechanism 24a to the outside, and CIP was performed in the upstream-side circulation system 25a. At that time, as the first rinsing step, water having a temperature of 15° C. was supplied first to the upstream-side circulation system 25a for 5 minutes.

Next, as the chemical circulation step, a chemical was supplied and circulated in the upstream-side circulation system 25a. At that time, the chemical was supplied and circulated in the upstream-side circulation system 25a for 15 minutes. In addition, at that time, an alkaline cleaning solution containing sodium hydroxide in an amount of 2% by mass was used as the chemical. The temperature of the chemical heated by the holding tube 33 of the UHT 3 was 140° C.

Next, as the second rinsing step, water was supplied to the upstream-side circulation system 25a for 10 minutes. At that time, the temperature of the water heated by the holding tube 33 of the UHT 3 was 140° C.

Next, as the third rinsing step, water having a temperature of 15° C. was supplied to the upstream-side circulation system 25a for 10 minutes. In addition, the water used at the third rinsing step was collected to obtain sample data.

The contents of ethyl butyrate, ethyl 2-methylbutyrate, and limonene, which are representative flavors, contained in the obtained sample data were measured (Table 1).

Comparative Example

CIP was performed in the upstream-side circulation system 25a as in the example except that, at the chemical circulation step, the temperature of the chemical heated by the holding tube 33 of the UHT 3 was 80° C., water having a temperature of 15° C. was supplied to the upstream-side circulation system 25a for 20 minutes as the second rinsing step, the water used at the second rinsing step was collected to obtain sample data, and the third rinsing step was not performed. The contents of ethyl butyrate, ethyl 2-methylbutyrate, and limonene contained in the obtained sample data were measured (Table 1).

TABLE 1

|  | Ethyl butyrate (%) | Ethyl 2-methylbutyrate (%) | Limonene (%) |
|---|---|---|---|
| Example | 19 | 33 | 75 |
| Comparative example | 100 | 100 | 100 |

Table 1 indicates ratios of the contents of ethyl butyrate, ethyl 2-methylbutyrate, and limonene contained in the sample data obtained in the example to the contents of ethyl butyrate, ethyl 2-methylbutyrate, and limonene contained in the sample data obtained in the comparative example.

As illustrated in Table 1, in the example, the content of ethyl butyrate contained in rinse water was 19% relative to the comparative example. In addition, in the example, the content of ethyl 2-methylbutyrate contained in rinse water was 33% relative to the comparative example. Furthermore, the content of limonene contained in rinse water was 75% relative to the comparative example.

Consequently, the flavors remaining in the upstream-side circulation system 25a can be efficiently removed in the example. In particular, by heating water to a temperature of 140° C. at the second rinsing step, the water-soluble flavor remaining in the upstream-side circulation system 25a can be efficiently removed.

It is possible to appropriately combine a plurality of constituent elements disclosed in the above embodiments and modifications as necessary. Alternatively, some constituent elements may be omitted from all the constituent elements described in the above embodiments and modifications.

The invention claimed is:

1. A deodorizing method of deodorizing a filling system, the deodorizing method comprising:
    a first CIP step of performing CIP of a first circulation system including a product heating sterilizer that heats a drink to a heated drink temperature in a range of 60° C. to 150° C., a product supply system pipe including a plurality of upstream-side supply pipes through which the drink is to be passed, and a packing provided at a connection point between the upstream-side supply pipes, the plurality of upstream-side supply pipes being connected to each other in series;
    a first SIP step of performing SIP of the first circulation system;
    a second CIP step of performing CIP of a second circulation system including a filling device that fills a content in a vessel;
    a second SIP step of performing SIP of the second circulation system;
    a step of cooling the second circulation system after a second SIP step; and
    a deodorizing treatment step of performing a deodorizing treatment on the first circulation system and the second circulation system,
    wherein the step of cooling the second circulation system includes a step of cooling the second circulation system with aseptic air, and a step of cooling the second circulation system, which has been cooled with aseptic air, with aseptic water,
    wherein the deodorizing treatment step includes a step of supplying water in a flow path of the first circulation system which has been subjected to the first SIP, a step of heating the water supplied to the first circulation system by the product heating sterilizer, and a step of supplying the water heated by the product heating sterilizer in a flow path of the second circulation system which has been subjected to the step of cooling the second circulation system
    wherein, in the second SIP step, steam is supplied to the second circulation system at a temperature in a range of 90° C. to 150° C.,
    wherein, in the step of cooling the second circulation system with aseptic air, the second circulation system is cooled to a temperature in a range of 60° C. to 100° C., and
    wherein, in the deodorizing treatment step, a temperature of the water supplied to the first circulation system is equal to or higher than the heated drink temperature, and thus the packing is thermally expanded by the water, and the water enters a gap formed between the packing and the upstream-side supply pipe due to thermal expansion of the packing.

2. The deodorizing method according to claim 1, wherein in the step of supplying water to the first circulation system having been subjected to the first SIP, a time required to supply the water is in a range of 5 minutes to 120 minutes.

3. The deodorizing method according to claim 1, wherein in the step of supplying the water heated by the product heating sterilizer to the second circulation system having been subjected to the second SIP, a time required to supply the water to the second circulation system is in a range of 5 minutes to 120 minutes.

4. A deodorizing method of deodorizing a filling system, the deodorizing method comprising:
    a first CIP step of performing CIP of a first circulation system including a product heating sterilizer that heats a drink to a heated drink temperature in a range of 60° C. to 150° C.;
    a first SIP step of performing SIP of the first circulation system;
    a second CIP step of performing CIP of a second circulation system including a product supply system pipe including a plurality of downstream-side supply pipes through which a content is to be passed, a packing which is made of ethylene propylene diene rubber and which is provided at a connection point between the downstream-side supply pipes, and a filling device that fills the content in a vessel, the plurality of downstream-side supply pipes being connected to each other in series;
    a second SIP step of performing SIP of the second circulation system;
    a step of cooling the second circulation system after the second SIP step; and
    a deodorizing treatment step of performing a deodorizing treatment on at least the second circulation system from among the first circulation system and the second circulation system,
    wherein the step of cooling the second circulation system includes a step of cooling the second circulation system with aseptic air, and a step of cooling the second circulation system, which has been cooled with aseptic air, with aseptic water,
    wherein the second circulation system includes a tank that stores a sterilized drink and a heat sterilizer for preparing aseptic water that is connected to a downstream side of the tank and prepares aseptic water,
    wherein the deodorizing treatment step includes a step of supplying water to the heat sterilizer for preparing aseptic water and heating the water, and a step of supplying the water heated by the heat sterilizer for preparing aseptic water in a flow path of the second circulation system having been subjected to the step of cooling the second circulation system,
    wherein, in the second SIP step, steam is supplied to the second circulation system at a temperature in a range of 90° C. to 150° C.,
    wherein, in the step of cooling the second circulation system with aseptic air, the second circulation system is cooled to a temperature in a range of 60° C. to 100° C., and
    wherein, in the step of supplying the water to the heat sterilizer for preparing aseptic water and heating the water, the water is heated to a temperature in a range of 70° C. to 100° C., and thus the packing is thermally expanded, and the water enters a gap formed between the packing and the downstream-side supply pipe due to thermal expansion of the packing.

5. The deodorizing method according to claim 4, wherein in the step of supplying the water heated by the heat sterilizer for preparing aseptic water to the second circulation system having been subjected to the second SIP, a time required to supply the water to the second circulation system is in a range of 5 minutes to 120 minutes.

\* \* \* \* \*